(12) United States Patent
Zigel et al.

(10) Patent No.: US 11,672,472 B2
(45) Date of Patent: Jun. 13, 2023

(54) METHODS AND SYSTEMS FOR ESTIMATION OF OBSTRUCTIVE SLEEP APNEA SEVERITY IN WAKE SUBJECTS BY MULTIPLE SPEECH ANALYSES

(71) Applicants: B.G. NEGEV TECHNOLOGIES AND APPLICATIONS LTD., AT BEN-GURION UNIVERSITY, Beer-Sheva (IL); MOR RESEARCH APPLICATIONS LTD., Tel Aviv (IL)

(72) Inventors: Yaniv Zigel, Omer (IL); Dvir Ben Or, Gedera (IL); Ariel Tarasiuk, Meitar (IL); Eliran Dafna, Beer-Sheva (IL)

(73) Assignees: B.G. NEGEV TECHNOLOGIES AND APPLICATIONS LTD., AT BEN-GURION UNIVERSITY, Beer-Sheva (IL); MOR RESEARCH APPLICATIONS LTD., Tel Aviv (IL)

( * ) Notice: Subject to any disclaimer, the term of this patent is extended or adjusted under 35 U.S.C. 154(b) by 519 days.

(21) Appl. No.: 16/316,395

(22) PCT Filed: Jul. 10, 2017

(86) PCT No.: PCT/IL2017/050779
§ 371 (c)(1),
(2) Date: Jan. 9, 2019

(87) PCT Pub. No.: WO2018/011794
PCT Pub. Date: Jan. 18, 2018

(65) Prior Publication Data
US 2019/0298271 A1    Oct. 3, 2019

Related U.S. Application Data

(60) Provisional application No. 62/360,400, filed on Jul. 10, 2016.

(51) Int. Cl.
*A61B 5/00* (2006.01)
*G16H 50/30* (2018.01)
(Continued)

(52) U.S. Cl.
CPC .......... *A61B 5/4818* (2013.01); *A61B 5/4803* (2013.01); *A61B 5/4842* (2013.01);
(Continued)

(58) Field of Classification Search
CPC .... G16H 50/30; A61B 5/4803; A61B 5/4818; A61B 5/7267; A61B 5/7278; A61B 5/0826
See application file for complete search history.

(56) References Cited

U.S. PATENT DOCUMENTS 5,751,904 A * 5/1998 Inazumi .................. G10L 15/16
704/232
2008/0147391 A1* 6/2008 Jeong ...................... G10L 15/02
704/232

(Continued)

FOREIGN PATENT DOCUMENTS

WO    WO 2014/115115    7/2014

OTHER PUBLICATIONS

Fiz et al. "Acoustic Analysis of Vowel Emission in Obstructive Sleep Apnea." Chest. Oct. 1993;104(4):1093-6. (Year: 1993).*
(Continued)

*Primary Examiner* — Meredith Weare
(74) *Attorney, Agent, or Firm* — Nixon & Vanderhye PC

(57) ABSTRACT

Provided herein is a method and system for the estimation of apnea-hypopnea index (AHI), as an indicator for Obstructive sleep apnea (OSA) severity, by combining speech descriptors from three separate and distinct speech signal domains. These domains include the acoustic short-term features (STF) of continuous speech, the long-term features
(Continued)

(LTF) of continuous speech, and features of sustained vowels (SVF). Combining these speech descriptors may provide the ability to estimate the severity of OSA using statistical learning and speech analysis approaches.

16 Claims, 3 Drawing Sheets

(51) Int. Cl.
    *A61B 7/00*         (2006.01)
    *G16H 50/20*      (2018.01)
    *G16H 50/50*      (2018.01)

(52) U.S. Cl.
    CPC .......... *A61B 5/7267* (2013.01); *A61B 5/7275* (2013.01); *A61B 5/7278* (2013.01); *A61B 7/003* (2013.01); *G16H 50/30* (2018.01); *G16H 50/20* (2018.01); *G16H 50/50* (2018.01)

(56) References Cited

U.S. PATENT DOCUMENTS

| | | | |
|---|---|---|---|
| 2014/0200474 A1* | 7/2014 | Selvaraj | A61B 5/087 600/529 |
| 2014/0276228 A1* | 9/2014 | De Waele | A61B 5/1075 600/586 |
| 2015/0351663 A1 | 12/2015 | Zigel et al. | |

OTHER PUBLICATIONS

Kriboy et al. "Detection of Obstructive Sleep Apnea in Awake Subjects by Exploiting Body Posture Effects on the Speech Signal." Annu Int Conf IEEE Eng Med Biol Soc. 2014;2014:4224-7. (Year: 2014).*
Gomez-Garcia et al. "GMM-based Classifiers for the Automatic Detection of Obstructive Sleep Apnea." In Proceedings of the International Conference on Bio-inspired Systems and Signal Processing (BIOSIGNALS-2013), pp. 364-367. (Year: 2013).*
Espinoza-Cuadros et al. "Reviewing the connection between speech and obstructive sleep apnea." Biomed Eng Online. Feb. 20, 2016;15:20. (Year: 2016).*
Elisha et al., "Detection of Obstructive Sleep Apnea Using Speech Signal Analysis" *Maveba*, 4 pages (2011).
Ferri et al., "Comparative Study of Techniques for Large-Scale Feature Selection" *Pattern Recognition in Practice IV*, pp. 403-413 (1994).
Fox et al., "Speech Dysfunction of Obstructive Sleep Apnea" *Chest Journal*, vol. 96, No. 3: 589-595 (Sep. 1989).
International Search Report issued in PCT/IL2017/050779 dated Oct. 24, 2017.
Jakovljević et al., "Energy Normalization in Automatic Speech Recognition" *International Conference on Text, Speech and Dialogue*, pp. 341-347 (2008).
Kinnunen et al., "What Else is New Than the Hamming Window? Robust MFCCs for Speaker Recognition via Multitapering" *Interspeech*, pp. 2734-2737 (Sep. 26-30, 2010).
Or et al., "Obstructive Sleep Apnea Severity Estimation: Fusion of Speech-Based Systems" *38$^{th}$ Annual International Conference of the IEEE*, pp. 3207-3210 (2016).
Pudil et al., "Floating search methods in feature selection" *Pattern Recognition Letters*, vol. 15: 1119-1125 (Nov. 1994).
Qi et al., "Auditory Features Based on Gammatone Filters for Robust Speech Recognition" *IEEE International Symposium on Circuits and Systems*, 4 pages, (2013).
Reynolds, "Speaker Verification Using Adapted Gaussian Mixture Models" *Digital Signal Processing*, vol. 10: 19-41 (2000).
Riedel et al., "Minimum bias multiple taper spectral estimation" *IEEE Transactions on Signal Processing*, vol. 43, No. 1: 188-195 (1995).
Robb et al., "Vocal Tract Resonance Characteristics of Adults with Obstructive Sleep Apnea" *Acta Oto-Laryngologica*, vol. 117: 760-763 (1997).
Sadjadi et al., "Mean Hilbert Envelope Coefficients (MHEC) for Robust Speaker Recognition" *Interspeech*, 4 pages, (2012).
Sohn et al., "A Statistical Model-Based Voice Activity Detection" *IEEE Signal Processing Letters*, vol. 6, No. 1: 1-3 (Jan. 1999).
Thomson, "Spectrum Estimation and Harmonic Analysis" *Proceedings of the IEEE*, vol. 70, No. 9: 1055-1096 (Sep. 1982).
Wu et al., "Automatic Recognition of Speech Emotion Using Long-Term Spectro-Temporal Features" *16th International Conference on Digital Signal Processing, IEEE*, 6 pages, (2009).
Yumoto et al. "Harmonics-to-noise ratio as an index of the degree of hoarseness" *J. Acoust. Soc. Am.*, vol. 71, No. 6: 1544-1550 (1982).

* cited by examiner

METHODS AND SYSTEMS FOR ESTIMATION OF OBSTRUCTIVE SLEEP APNEA SEVERITY IN WAKE SUBJECTS BY MULTIPLE SPEECH ANALYSES

This application is the U.S. national phase of International Application No. PCT/IL2017/050779 filed 10 Jul. 2017, which designated the U.S. and claims the benefit of U.S. Application No. 62/360,400 filed 10 Jul. 2016, the entire contents of each of which are hereby incorporated by reference.

FIELD OF THE INVENTION

The present invention pertains to the field of sleep disorders, in particular, to estimation of obstructive sleep apnea severity in a wake patient in need thereof by providing for said patient a value of apnea-hypopnea index (AHI). The value is provided by the methods and systems as described herein, by multiple speech analyses.

BACKGROUND OF THE INVENTION

Obstructive sleep apnea (OSA) is characterized by repetitive partial or complete cessations of airflow, due to upper airway collapsibility. The estimated prevalence of OSA among adults is between 5% and 14%. However, this condition is often unrecognized and under-diagnosed. Apart from being a common sleep-related breathing disorder, OSA is a risk factor for both chronic and acute conditions, such as cardiovascular events, excessive daytime sleepiness, and car accidents.

The severity of OSA is assessed by calculating the apnea-hypopnea index (AHI), which is the number of apnea and hypopnea events for each hour of sleep during an overnight polysomnography (PSG) study. Typically, AHI≤5 is not regarded as OSA, with mild sleep apnea being diagnosed at AHI between 5 and 15, moderate between 15 and 30, and severe sleep apnea is usually diagnosed at AHI over 30.

The ability to assess OSA during wakefulness was explored using tracheal breath sounds analysis, as it was established that OSA is associated with anatomical and functional abnormalities of the upper airway, leading to alterations of vocal tract physiology and structural changes of soft tissues, collectively affecting the acoustic characteristics of speech. The speech characteristics of OSA patients might therefore differ from those of non-OSA subjects. Irregularities in phonation, articulation, and resonance were implicated in OSA patients, e.g. in the publication of A. Fox, P. Monoson, and C. D. Morgan, "Speech dysfunction of obstructive sleep apnea. A discriminant analysis of its descriptors," Chest Journal, vol. 96, pp. 589-595, 1989. Differences in formant frequencies and bandwidths were found when examining sustained vowels of OSA patients and non-OSA speakers, e.g. in the publication by Robb, M., J. Yates and E. Morgan (1997), "Vocal tract resonance characteristics of adults with obstructive sleep apnea." Acta oto-laryngologica 117(5): 760-763. Speech descriptors were therefore used, utilizing machine learning techniques, in order to apply OSA/non-OSA classification schemes, e.g. in the publication O. Elisha, A. Tarasiuk, and Y. Zigel, "Detection of obstructive sleep apnea using speech signal analysis," in MAVEBA, 2011, pp. 13-16. A method of determining a value of AHI in speaking subject by analyzing specific phonemes was also disclosed in PCT publication WO/2014/115115.

PSG requires considerable technical expertise, it is labor intense, time consuming, and it may cause discomfort to the patient. These, among other disadvantages, create the need for alternative, simple, and cost-effective approaches for OSA screening and severity estimation, preferably in wake subjects. There is also a need for a method and systems for OSA severity estimation, regardless of peculiarities of specific phonemes' dialectal and other natural linguistic differences between the subjects, speaking their native or a foreign language.

SUMMARY OF THE INVENTION

Provided herein is a system for the estimation of AHI, as an indicator for OSA severity, by combining speech descriptors from three separate and distinct speech signal domains. These domains include the acoustic short-term features (STF) of continuous speech, the long-term features (LTF) of continuous speech, and features of sustained vowels (SVF). Combining these speech descriptors may provide the ability to estimate the severity of OSA using statistical learning and speech analysis approaches.

Also provided herein a method of estimation of AHI, as an indicator for OSA severity, comprising obtaining acoustic data from a subject, extracting descriptors of the acoustic short-term features (STF) of continuous speech, the long-term features (LTF) of continuous speech, and features of sustained vowels (SVF), obtaining AHI estimates from each set of descriptor features, and combining said AHI estimates to furnish an improved fused AHI estimate. Combining these speech descriptors may provide the ability to estimate the severity of OSA using statistical learning and speech analysis approaches.

The present invention relates to a method and system for obtaining audio recorded phonogram signals and processing said signals to obtain an AHI of the recorded subject. The recorded phonograms may be of a subject speaking and/or of a subject uttering sound. The signals are processed in order to obtain an AHI estimate of the recorded subject. The signal processing comprises obtaining groups of features derived from the signals and inputting them into a preformed computing models applied thereto. The outputs of the models are inputted into a fusing model that calculates the final AHI estimate score.

The present invention relates to a method for determining apnea-hypopnea index estimation of a wake subject, said method comprising:
- obtaining an audio recorded phonogram signal comprising a speech segment and/or an audio recorded phonogram signal comprising a sustained-vowel segment;
- framing said signal comprising a sustained-vowel segment into frames;
- framing said signal comprising a speech segment into a set of long term frames and into a set of short term frames;
- generating one or more feature parameters for each short term frame, that are associated with short term characteristics and that are calculated according to the frame signal or according to a signal generated from the frame signal;
- generating one or more feature parameters for each long term frame, that are associated with long term characteristics and that are calculated according to the frame signal or according to a signal generated from the frame signal;
- generating one or more feature parameters for each sustained-vowel frame, that are associated with sustained-vowel characteristics and that are calculated according to the frame signal or according to a signal generated from the frame signal;

applying a first computing system preformed model on the generated short term parameters to obtain a short term score;

applying a second computing system preformed model on the generated long term parameters to obtain a long term score;

applying a third computing system preformed model on the generated sustained-vowel parameters to obtain a sustained-vowel score;

applying a fusing model on the short term score and on the long term score and on the sustained-vowel score to obtain said subject's apnea-hypopnea index estimation.

Preferably, the method further comprises carrying out a pre-processing stage comprising noise reduction of the signal comprising a speech segment and/or of the signal comprising a sustained-vowel segment.

Preferably, the method further comprises obtaining a universal background Gaussian mixture model (GMM-UBN) vector comprising short term features corresponding to the subject's short term features, and modifying said GMM-UBN with said subject's short-term features to obtain a subject-specific distribution model vector; wherein the applying a computing system preformed model on the generated short term parameters comprises applying a computing system preformed model on said subject-specific distribution model vector to obtain the short term score.

Preferably, the method further comprises generating the computing system preformed models comprising:

obtaining an audio recorded phonogram signal comprising a speech segment and/or an audio recorded phonogram signal comprising a sustained-vowel segment for a plurality of subjects;

framing said signals comprising a sustained-vowel segment into frames;

framing said signal comprising a speech segment into a set of long term frames and into a set of short term frames;

generating one or more feature parameters for each short term frame, that are associated with short term characteristics and that are calculated according to the frame signal or according to a signal generated from the frame signal;

generating one or more feature parameters for each long term frame, that are associated with long term characteristics and that are calculated according to the frame signal or according to a signal generated from the frame signal;

generating one or more feature parameters for each sustained-vowel frame, that are associated with sustained-vowel characteristics and that are calculated according to the frame signal or according to a signal generated from the frame signal;

inputting the generated short term parameters of each subject into a first machine learning computing system along with corresponding true result annotated AHI scores to generate the first computing system preformed model according to machine learning;

inputting the generated long term parameters of each subject into a second machine learning computing system along with corresponding true result annotated AHI scores to generate the second computing system preformed model according to machine learning;

inputting the generated sustained-vowel parameters of each subject into a third machine learning computing system along with corresponding true result annotated AHI scores to generate the third computing system preformed model according to machine learning.

Preferably, the method further comprises obtaining a universal background Gaussian mixture model (GMM-UBN) vector comprising short term features corresponding to the subjects' short term features; modifying said GMM-UBN with said subjects' short-term features to obtain a subject-specific distribution model vector for each subject; wherein inputting the generated short term parameters of each subject into a first machine learning computing system comprises inputting said subject-specific distribution model vector for each subject.

Preferably, said short term features comprise in male speakers at least one of comprises gammatone-frequency $10^{th}$ cepstral coefficient ($GFCC_{10}$), first time derivative of Thomson multitaper mel-frequency $9^{th}$ cepstral coefficient ($\Delta c_9$), mean Hilbert envelope $11^{th}$ coefficient ($MHEC_{11}$), $GFCC_7$, sine-wave cepstrum $3^{rd}$ estimator ($SWCE_3$) and Thomson multitaper mel-frequency $9^{th}$ cepstral coefficient ($c_9$).

Preferably, said short term features in female subjects comprise at least one of $SWCE_{12}$, $MHEC_7$, $\Delta\Delta c_{12}$, and $\Delta\Delta c_{16}$.

Preferably, said long term features comprise in male speakers at least one of an arithmetic mean of a first time derivative of spectro-temporal energy $\Delta\Phi^{(3)}$, an inter-quantile range of second time derivative of linear prediction cepstral coefficients $\Delta\Delta LPCC_1^{(1)}$, a variance of $LPCC_3^{(3)}$, an inter-quantile range of $LPCC_3^{(3)}$, and an inter-quantile range of $LPCC_3^{(1)}$.

Preferably, said long term features in female subjects comprise at least one of a variance of $LPCC_4^{(3)}$, a variance of $LPCC_4^{(1)}$, variance of $\Phi^{(3)}$, and an arithmetic mean of $LPCC_1^{(2)}$.

Preferably, said sustained vowel features comprise in male speakers at least one of a "u:" phoneme arithmetic mean of soft phonation index (SPI), an "e" phoneme geometric mean of spectral flatness, a "u:" phoneme zero crossing rate of the first time derivative of mel-frequency cepstral coefficient $\Delta MFCC_1$, an "ɒ" phoneme zero crossing rate of $\Delta MFCC_2$, and an "ɒ" phoneme inter-quartile range of $\Delta MFCC_4$.

Preferably, said sustained vowel features in female subjects comprise at least one of an "ɒ" phoneme skewness of $MFCC_5$, an "a:" phoneme maximum of spectral flatness, an "e" phoneme arithmetic mean of 3-point Amplitude perturbation quotient (APQ3), an "a:" phoneme quadratic mean of shimmer, and an "i" phoneme second quartile of $MFCC_{12}$.

The present invention relates to a system for determining apnea-hypopnea index estimation of a wake subject, comprising:

a processor;

a memory coupled to the processor and configured to store program instructions executable by the processor to implement the method for determining apnea-hypopnea index estimation of a wake subject, said method comprising:

obtaining an audio recorded phonogram signal comprising a speech segment and/or an audio recorded phonogram signal comprising a sustained-vowel segment;

framing said signal comprising a sustained-vowel segment into frames;

framing said signal comprising a speech segment into a set of long term frames and into a set of short term frames;

generating one or more feature parameters for each short term frame, that are associated with short term characteristics and that are calculated according to the frame signal or according to a signal generated from the frame signal;

generating one or more feature parameters for each long term frame, that are associated with long term characteristics and that are calculated according to the frame signal or according to a signal generated from the frame signal;

generating one or more feature parameters for each sustained-vowel frame, that are associated with sustained-vowel characteristics and that are calculated according to the frame signal or according to a signal generated from the frame signal;

applying a first computing system preformed model on the generated short term parameters to obtain a short term score;

applying a second computing system preformed model on the generated long term parameters to obtain a long term score;

applying a third computing system preformed model on the generated sustained-vowel parameters to obtain a sustained-vowel score;

applying a fusing model on the short term score and on the long term score and on the sustained-vowel score to obtain said subject's apnea-hypopnea index estimation.

DETAILED DESCRIPTION OF THE INVENTION

Figure 1:
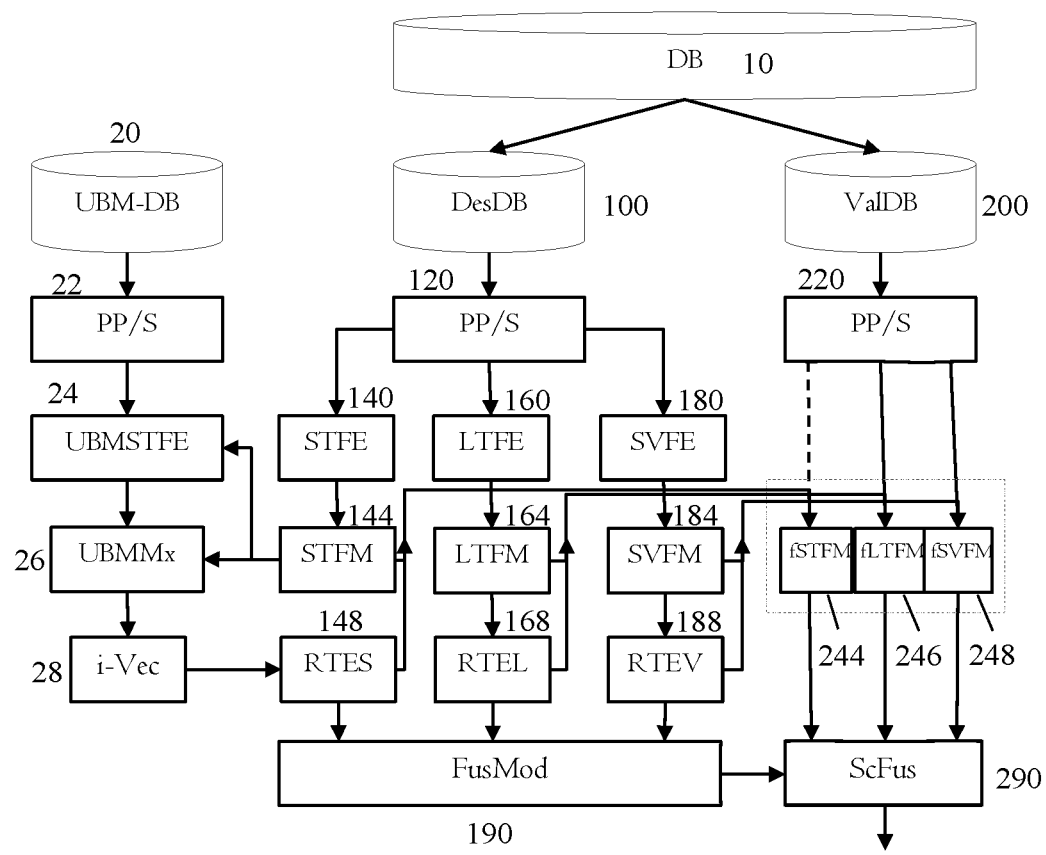
FIG. 1 schematically demonstrates a flow chart for training a system for providing an estimate of AHI to a wake subject according to one embodiment of the invention.

The present invention relates to a system for diagnosing the severity of obstructive sleep apnea, in wake subject in need thereof, by providing an estimation of apnea-hypopnea index of said subject. The present invention system comprises a recorder device preferably with a microphone. The microphone is configured to register sounds made by the person. Various recorders may be used. An example of a digital audio recorder device is model EDIROL R-4 (Roland, 2-7 Kandasuda-cho, Chiyoda-ku, Tokyo 101-0041, Japan). An example of a microphone is ambient microphone RØDE NTG-1 (107 Carnarvon St, Silverwater, NSW, 2128 Australia).

The microphone (and recorder) transmits the sounds that it registers to a computer system. The computer system comprises a processor configured to process the voice sound signals. The computer system comprises a memory in which it stores the speech sound signals that the computer system receives from the microphone. The computer system (e.g. by use of the processor) is configured to carry out computer executable instruction sets relating to at least one operation selected from pre-processing, noise reduction, segmentation, feature extraction, model estimation, and data comparison to a preformed model, carrying out machine learning tasks (e.g. classification), as explained herein.

The computer system may comprise a PC, a smart phone, a laptop, and/or a work book that stores and executes the instruction sets defined herein. However, the computer system is not limited to being housed in a single computer, or a computer located in a same room with the sleeping person. Computer system may be a distributed system having components and executable instruction sets located in different servers, and may be partially or completely based on access to servers via the internet, that is partially or completely "cloud based". An audio signal is a representation of sound, typically as an electrical voltage. Audio signals may be characterized by parameters such as their bandwidth, power level, e.g. in decibels (dB), and voltage level.

In one aspect, the present invention is drawn to a method of diagnosing the severity of obstructive sleep apnea, in wake subject in need thereof, by providing an estimation of apnea-hypopnea index of said subject. The estimation of AHI may usually be correlative to the evaluation performed on the same subject using polysomnography (PSG) technique as known in the art.

In one embodiment, to practice the diagnosing the severity of obstructive sleep apnea, in wake subject in need thereof, by providing an estimation of apnea-hypopnea index of said subject, the computer system may be trained as known in the art of machine learning and described in greater detail herein below. The training may comprise fitting a classifier model or a regression model, which provides an acceptable correlation with the results obtained by PSG. The training may furnish a pre-formed model, also termed as "fitted model" and the like, as used interchangeably herein.

The method may comprise a step of obtaining a phonogram of subject's voice. The present invention may comprise recording the subject's voice. The phonogram may usually comprise several distinct parts. In one embodiment, the phonogram comprises the recording of subject's utterance of sustained vowels. The term "sustained" as used herein in reference to the vowels uttered by the subject for production of said subject's phonogram should be construed as uttering a vowel sound as described herein, for a period of at least 1 second, preferably at least 2 seconds, and may be at least 3 seconds, at least 4 seconds, at least 5 seconds, or of any other suitable duration, e.g. between 1 and 10 seconds, or between 2 and 9 seconds, or between 4 and 6 seconds. The vowel sounds are usually phonemes natural to the language the subject speaks as a native language, or as a fluent speaker of a foreign language. By the way of example, the vowels may comprise phonemes "a:", "i:", "u:", "e", and "ɒ", as expressed by International Phonetic Alphabet. Preferably, the recording of utterance of sustained vowels comprises a set of phonemes, e.g. comprising all vowel phonemes of the subject's language. By the way of example, for English or Hebrew native or fluent foreign speakers, the set of phonemes includes any one of "a:", "e", "i:", "ɒ", and "u:". While these ubiquitous phonemes may be used universally, some other language-specific phonemes may also be employed.

The phonogram of subject's speech may also comprise recording of subject's utterance of a particular speaking protocol, in subject's native or fluent foreign language. The length of the speaking protocol may be from about 30 seconds to about 5 minutes (and may be possibly less). Preferably, the protocol is designed to last between 45 seconds and 4 minutes, or between 50 seconds and 3 minutes, or between 50 seconds and 2 minutes, or between 1 minute and 2 minutes, inclusive. The speaking protocol may be designed to include particular phonemes and phoneme sequences, e.g. "ma", and " [p". The speaking protocol may be arranged in sentences to facilitate the utterance by the tested subject. The sentences may usually be chosen such that the subject would utter the sentence using a single breath. Alternatively, the length of the sentence may be long enough to require the subject to inhale during a break in the middle of the sentence. The protocol may also comprise sentences of variable duration. Usually, the length of the sentences is chosen between 6 and 18 phonemes for short sentences, and between 19 and 40 phonemes for long sentences. The number of sentences in the protocol may be governed by the length of the intended recording, and may optionally vary from 10 to 20 short sentences and optionally from 5 to 15 of long sentences.

Additionally or alternatively, the speaking protocol may comprise standalone syllables and/or logatomes. The suitable syllables may include, inter alia, "ml", and "ze". The suitable logatomes may include, inter alia, "fe", and "do".

The phonogram may be obtained by any suitable sound recording device as known in the art. Generally, the analog speech signal may be sampled and quantized in order to provide a digital signal, suitable for digital processing. The digitizing may usually be executed prior to practical processing by the recording device, and the digitizing procedure parameters (such as number of bits, quantization method, and sampling rate) may vary among different recording setups. The recording devices may be, e.g. by "H4" Handy recorder, manufactured by "ZOOM", Japan. Usually, the recorded phonogram may be in a form of a digital signal, e.g. of 16 to 96 kHz, e.g. 44.1 kilohertz, usually at a bit rate of 16 to 24, e.g. 16 bits per sample. Alternatively, the phonogram may be digitized by converting a suitable analog signal phonogram into digital signal format. Examples of suitable digital signal formats include, inter alia, *.wav, and *.aiff, as known in the art.

The methods of the present invention may further comprise a step of pre-processing the obtained phonogram of a subject's voice. The pre-processing may include any one of the following steps and combinations thereof: a removing of DC component, a removing of non-speech segments, a detecting of voice activity, a normalizing of the signal energy, a filtering of pre-emphasis, a framing into time-frames, and into windowing the signal using a suitable window function.

Suitable means for a removing of DC component include, but not limited to subtraction of the acquired signal average value, e.g. by measuring and subtracting the DC component generated by the recording device and its inner amplifiers from the analyzed signal.

Suitable means for a detecting of voice activity include, but not limited to a method described in the publication Sohn, J., N. S. Kim and W. Sung (1999). "A statistical model-based voice activity detection." IEEE signal processing letters 6(1): 1-3.

Suitable means for a removing of non-speech include, but not limited to identifying segments with voice activity and ignoring the other segments, e.g. by assigning zero values thereto, or by excluding the segments without detected voice activity from further processing and analysis.

Suitable means for a normalizing of the signal energy include, but not limited to a method described in the publication Jakovljević, Nikša, et al. "Energy normalization in automatic speech recognition." International Conference on Text, Speech and Dialogue. Springer, Berlin, Heidelberg, 2008.

The framing may be performed as known in the art. The length of the frames may be chosen according to the need, but may usually be either a short frame or a long frame. The short frame may optionally have a duration of between 10 and 50 milliseconds (ms), e.g. 15 ms, 17 ms, 20 ms, 25 ms, 30 ms, 35 ms, 40 ms, 45 ms, or 50 ms, or between any value therebetween, e.g. between 10 and 45 ms, between 15 and 40 ms, or between 25 and 35 ms. The long frame may optionally have duration of longer than about 30 ms, e.g. 128 to 512 ms, or between 240 and 270 ms, e.g. 256 ms. Sequential frames may optionally have an overlap (frame shift), between 10 to 90% of the frame duration, preferably between 25 and 60% of the frame duration, such that a frame duration is covered separately by several frame intervals. Usually, the frame shift of a short frame is between 5 and 15 ms, e.g. 10 ms. The frame shift of a long frame may thus optionally be between 20 and 80 ms, or between 60 and 70 ms, e.g. 64 ms. Windowing function may be applied to effect signal framing, e.g. Hamming window function. Other window functions suitable for pre-processing of the signal include, but not limited to Blackman window and Hann window functions.

The phonogram may be further segmented into the typical components (segments) of the speaking protocol, e.g. into the sustained vowel segment, into fluent speech segment, into syllables segment, into logatomes segments, in accordance with the composition of the speaking protocol. The segmenting may be performed manually. The segmenting may also be carried out by recording separately the segments of the speaking protocol. The segmenting may also be performed automatically, e.g. by a user-interface-guided application that prompts the user to read each part of the protocol separately, thereby allowing an optionally coupled recording device to record these distinct segment separately by design. In some embodiments, the phonogram may be segmented into a sustained vowel segment, and into a segment comprising the remainder of the speech protocol.

The segments of the speech protocol may be processed to extract features. The term "feature", as used herein in reference to the speech processing techniques, should be construed as a value or a set of values directly deductible from the subject's phonogram. The means to directly deduce the value or the set of values may be dependent on a specific feature, and is usually performed by performing a mathematical transformation on the values of spectral and/or gain and/or temporal and/or cepstral components of the phonogram (speech waveform), as generally known in the field of speech processing. The feature extraction may be typically performed in a specific time frame level. The features usually provide a compact description of the speech waveform.

The methods of the present invention may further comprise a step of obtaining an anthropometric data of said subject. The anthropometric data may include at least one of gender, weight, height, age, or body-mass index (BMI) of the subject. The anthropometric data may also comprise diagnostic results of a variety of medical tests, including but not limited to, an apnea-hypopnea index as provided by PSG. The anthropometric data may usually be linked to a specific phonogram signal or to a plurality of phonogram signals.

The computing may be adapted to perform classification and machine learning tasks to generate model, sort features or other means to fit data. In every instance wherein a specific computing model is named, it may be evident to the skilled artisan that many alternatives and equivalents may be possible. The mentioned and/or exemplified methods and models are shown in connection with specific embodiments of the present disclosure may under certain circumstances be substituted with equivalent methodology.

A plurality of features is extracted from the subject's phonogram signal, and may usually be features and combinations of features that are correlative to the severity of the OSA. The combinations of features may be selected using a suitable regression model adapted to furnish correlation versus a standard test, e.g. a polysomnogram. The combinations of features may be processed together as a set of features, e.g. the sets of features may be further processed by a suitable regression technique, e.g. by an ensemble of regression trees, to provide an estimation of AHI score. In one embodiment of the present invention, the scores may be obtained by at least two techniques, preferably by three techniques as described herein, and their values may be fused together, e.g. by an elastic net regression model, to provide a fused AHI score. Alternatively or additionally, a feature obtained from one technique may be employed to enhance the correlation obtained by any other technique.

In one embodiment, a set of features extracted from the phonogram signal comprises short term features (STF). The STF are extracted by framing an appropriate segment of phonogram with short frames. The short frames may optionally have a duration of about 30 ms, and a frame shift optionally of about 15 ms. It has been now found that STF suitable for the OSA evaluation include a set of features. In one embodiment, the STF set suitable for OSA evaluation in male speakers comprises gammatone-frequency $10^{th}$ cepstral coefficient ($GFCC_{10}$), first time derivative of Thomson multitaper mel-frequency $9^{th}$ cepstral coefficient ($\Delta c_9$), mean Hilbert envelope $11^{th}$ coefficient ($MHEC_{11}$), $GFCC_7$, sine-wave cepstrum $3^{rd}$ estimator ($SWCE_3$) and Thomson multitaper mel-frequency $9^{th}$ cepstral coefficient ($c_9$). In a further embodiment, the STF set suitable for OSA evaluation in female speakers comprises $SWCE_{12}$, $MHEC_7$, $\Delta\Delta c_{12}$, and $\Delta\Delta c_{16}$. Without being bound by a theory it is believed that the inclusion of first and second time derivative features in the selected subsets, might reflect the alteration of the dynamics of the upper airways, which is associated with OSA.

Gammatone-frequency cepstral coefficients and their derivatives may be calculated, e.g. as described in the document Qi, J., D. Wang, Y. Jiang and R. Liu (2013). Auditory features based on gammatone filters for robust speech recognition. 2013 IEEE International Symposium on Circuits and Systems (ISCAS2013), IEEE. Thomson multitaper mel-frequency cepstral coefficients and their derivatives may be calculated, e.g. as described in the documents Thomson, D. J. (1982). "Spectrum estimation and harmonic analysis." Proceedings of the IEEE 70(9): 1055-1096, and Benesty, J., M. M. Sondhi and Y. Huang (2007). Springer handbook of speech processing, Springer Science & Business Media. Mean Hilbert envelope coefficients and their derivatives may be calculated, e.g. as described in the document Sadjadi, S. O., T. Hasan and J. H. Hansen (2012). Mean Hilbert Envelope Coefficients (MHEC) for Robust Speaker Recognition. INTERSPEECH. Sine-wave cepstrum estimators and their derivatives may be calculated, e.g. as described in the document Riedel, K. S. and A. Sidorenko (1995). "Minimum bias multiple taper spectral estimation." IEEE Transactions on Signal Processing 43(1): 188-195, or Kinnunen, T., R. Saeidi, J. Sandberg and M. Hansson-Sandsten (2010). What else is new than the hamming window? robust MFCCs for speaker recognition via multi-tapering. INTERSPEECH.

The discrete cepstrum is defined as the inverse discrete Fourier transform (DFT) of the log magnitude of the DFT of the signal: $c[n]=F^{-1}\{\log|F\{x[n]\}|\}$, where F is the DFT and $F^{-1}$ is the inverse discrete Fourier transform (IDFT). Cepstral analysis may be useful since it allows deconvolution of the signal into its components (source, filter, and radiation). Moreover, cepstral representation also offers compactness and orthogonality, whereas traditional linear prediction (LP), which are derived using auto-regressive (AR) modeling, are sensitive to numerical precision.

Thus, it may often be desirable to transform LP coefficients $\{a_n, G\}$ into cepstral coefficients $\{c_n\}$. This transform may be computed as follows $$c_n = \begin{cases} \ln(G), & n = 0 \\ a_n + \frac{1}{n}\sum_{k=1}^{n-1} kc_k a_{n-k} & 1 < n \le p \end{cases},$$

where n denotes the index of the cepstral coefficient to be computed, p is the order of the AR model, G is the gain of the model, and $a_n$ are the LP coefficients, e.g. achieved by solving Yule-Walker equations, e.g. by using Levinson-Durbin method.

The mel-frequency spectrum of a given discrete speech signal time-frame x[n], with a corresponding DFT X[k], is defined as $$MF[r] = \frac{1}{A_r}\sum_{k=L_r}^{U_r} |V_r[k]X[k]|, r = 1, \ldots, R,$$

where $V_r[k]$ is the triangular weighting function for the $r^{th}$ filter (out of R), ranging from DFT index $L_r$ to $U_r$, and $A_r$ serves as the normalization factor of the $r^{th}$ filter. Finally, for each time-frame, a discrete cosine transform (DCT) of the log-magnitude of the filter outputs is computed to obtain the MFCCs, as $$MFFC[m] = \frac{1}{R}\sum_{r=1}^{R} \log(MF[r])\cos\left[\frac{2\pi}{R}\left(r+\frac{1}{2}\right)m\right], m = 1, \ldots, M,$$

where M is the number of cepstral coefficients.

Commonly, the power spectrum of speech is estimated using the Hamming-windowed DFT, dictating that for the $m^{th}$ frame and $k^{th}$ frequency bin an estimate of the windowed periodogram can be expressed as $$\hat{S}(m, k) = \left|\sum_{j=0}^{N-1} w(j)s(m, j)e^{\frac{2\pi jk}{N}}\right|^2,$$

where $k \in \{0, 1, \ldots, K-1\}$ denotes the frequency bin index, N is the frame length, s(m, j) is the time domain speech signal and w(j) denotes the time domain window function called a taper, which usually is symmetric and decreases towards the frame boundaries. The usage of a window function (such as Hamming) does reduce the bias (difference between the estimated spectrum and the actual spectrum), but it does not reduce the variance of spectrum estimation, and consequently the variance of the computed MFCC features. Hence, it has been suggested replacing the windowed periodogram estimate by a so-called multi-taper spectrum estimate, formulated as follows $$\hat{S}_{MT}(m, k) = \frac{1}{M} \sum_{p=0}^{M-1} \lambda(p) \left| \sum_{j=0}^{N-1} w_p(j) s(m, j) e^{-\frac{2\pi jk}{N}} \right|^2,$$

where $w_p$ is the $p^{th}$ taper used for the spectral estimate $\hat{S}_{MT}(\cdot)$, which is also called the $p^{th}$ eigenspectrum, M denotes the number of tapers and $\lambda(p)$ is the weight corresponding to the $p^{th}$ taper (the tapers are chosen to be orthonormal). The multi-taper spectrum estimate is therefore obtained as the weighted average of M individual sub-spectra. Averaging these uncorrelated spectra gives a low variance spectrum estimate, and consequently low variance MFCC estimate.

Several sets of tapers have been proposed; a common one is composed of Slepian sequences (also called discrete prolate spheroidal sequences). This set of tapers is used to compute Thomson multi-taper MFCC. Another orthogonal family of tapers are the sine tapers, given by $$w_p(j) = \sqrt{\frac{2}{N+1}} \sin\left(\frac{\pi p(j+1)}{N+1}\right), j = 0, 1, \ldots, N-1.$$

This set of tapers is used to produce the sine weighted cepstrum estimator (SWCE). These sets of features have provided better performance compared to conventional MFCC, and yielded more improved robustness in speaker verification and recognition systems.

Gammatone frequency cepstral coefficients (GFCC) is a set of acoustic features used in developed automatic speaker recognition systems, in order to increase robustness to noisy environments (compared to the one achieved using conventional MFCC). The first step in the acquisition of GFCC is the computation of the gammatone cochleagram using a gammatone filterbank. The filters comprising this filterbank are equally distributed on Bark scale. Each gammatone filter is formulated as $g(t) = at^{n-1} e^{-2\pi bt} \cos(2\pi f_c t)$, where a sets the gain of the filter envelope, $f_c$ is the frequency of the amplitude modulator (central frequency of the filter), n is the order of the filter, and b is the decay factor. The next stage involves pre-emphasis of the acquired cochleagram, in order to reduce the dynamic range of the spectrum and intensify the frequency components which usually carry more speech-related information. Then, after averaging the absolute values of each filter output over a time frame duration, a loudness-compression is performed using cubic root operation. Finally, in order to overcome the fact that the overlapped form of the gammatone filters produces highly correlated features, similarly to the MFCC extraction procedure, a DCT is applied to the log-energy of each gammatone filter compressed output.

Mean Hilbert envelope coefficients (MHEC) and modulated sub-band energy is a set of features that may be an effective alternative to MFCCs for robust speaker identification and recognition under noisy and reverberant conditions. The extraction of MHEC also involves the usage of a gammatone filterbank (as in GFCC extraction), comprised of N filters (channels). Next, the focus is on slowly varying amplitude modulations rather than the fine structure; for this matter, the Hilbert temporal envelope of the $n^{th}$ channel (filter) output of the $k^{th}$ time frame, $\{s_k(n, i), 1 \leq n \leq N\}$, is then computed as the squared magnitude of the analytical signal, as follows $e_k(n, i) = s^2(n, i) + \hat{s}^2(n, i)$, where $\hat{s}(n, i)$ is the Hilbert transform of $s(n, i)$. The next step in the procedure is smoothing the obtained envelope representation using a low-pass filter, to further suppress remaining redundant high frequency components. Finally, after framing and windowing each smoothed envelope of each channel, a DCT is applied to obtain the MHEC representation. An additional application may utilize the Hilbert envelope representation of each gammatone channel output, in order to obtain a spectro-temporal representation. The procedure includes passing the set of Hilbert temporal envelopes, $\{e_k(n, i)\}$, through an M-band modulation filterbank (comprised of band-pass filters, to obtain $H_k(n, m, i)$. The spectro-temporal representation of the $k^{th}$ frame $E_k(n, m)$, is achieved by computing the energy of $H_k(n, m, i)$ across the temporal sample indices $\{1 \leq i \leq L\}$, where L is the time frame duration in samples, as $E_k(n, m) = \Sigma_{i=1}^{L} H_k^2(n, m, i)$. Finally, the spectro-temporal representation is used in order to compute $$\Phi_k^{(m)} = \frac{1}{N} \sum_{n=1}^{N} E_k(n, m),$$

which is the mean of the energy samples belonging to the $m^{th}$ modulation channel. $\Phi_k(m)$ gives a sense of the energy distribution in speech along the modulation frequency.

Additionally or alternatively, the following features may be extracted from the subject's phonogram.

Spectral centroid frequency (SCF) is the weighted average frequency for a given sub-band (or for the entire frequency range), where the weights are the normalized energy of each frequency component in the analyzed sub-band. It provides an approximation of the center of gravity of each sub-band, which is affected by the harmonic structure and pitch frequencies produced by the vocal source. Hence, SCF is affected by changes in pitch and harmonic structure. The SCF of the $b^{th}$ sub-band, $SCF_b$, is computed as $$SCF_b = \frac{\sum_{f=l_b}^{u_b} f |S[f]|}{\sum_{f=l_b}^{u_b} |S[f]|},$$

where S[f] is the analyzed spectrum.

Spectral centroid magnitude (SCM) is the weighted average magnitude for a given sub-band (or for the entire frequency range), where the weights are the weights are the frequencies of each magnitude bin in the analyzed sub-band, as $$SCM_b = \frac{\sum_{f=l_b}^{u_b} f |S[f]|}{\sum_{f=l_b}^{u_b} f}.$$

SCM captures, to a first order approximation, the distribution of energy in the analyzed sub-band. Both, SCF and SCM features, were used for performing speaker recognition with low equal error rate (EER).

Spectral flatness measure (SFM) as given below is a measure of the flatness of the spectrum. This measure might reveal phonation anomalies, as less harmonic signals will have a flatter spectrum. The SFM of the analyzed $b^{th}$ sub-band is calculated as the ratio between the geometric mean and the arithmetic mean of the power spectrum $$SFM_b = \frac{\left[\prod_{f=l_b}^{u_b} |S[f]|^2\right]^{1/(u_b-l_b+1)}}{(1/(u_b - l_b + 1)) \sum_{f=l_b}^{u_b} |S[f]|^2}.\backslash$$

Spectral crest factor as given below provides a measure for quantifying the tonality of the analyzed speech timeframe. It is useful for distinction of wideband from narrowband signals by indicating the normalized strength of the dominant peak in each sub-band $$Crest_b = \frac{\max(|S[f]|^2)}{(1/(u_b - l_b + 1)) \sum_{f=l_b}^{u_b} |S[f]|^2|}.$$

Spectral skewness gives a measure of the asymmetry of the spectrum around its centroid. As the skewness values are more negative (or positive) the spectrum has a more significant tail on the lower (or higher) frequencies compared to the centroid frequency. As spectral skewness approaches zero, the spectrum is more symmetric around its centroid.

Spectral kurtosis gives a measure of the flatness of the spectrum around its mean value. Kurtosis values above three indicate a peakier spectral distribution compared to normal distribution, whereas values below 3 indicate a flatter distribution.

Spectral entropy is used to capture the peaky characteristic of the spectral representation, and it is closely related to the amount of information present in the spectral content distribution. This measure is calculated as follows $$H(|S(f)|^2) = -\sum_{f=1}^{N} \left[\frac{|S[f]|^2}{\sum_{f=1}^{N} |S[f]|^2} \log\left(\frac{|S[f]|^2}{\sum_{f=1}^{N} |S[f]|^2}\right)\right],$$

where $|S(f)|^2$ is the power spectrum of the analyzed time frame. Low spectral entropy values indicate a more organic (harmonic) spectrum.

Spectral brightness reflects the amount of high frequency content, and is measured by relating the energy above a pre-defined cutoff frequency (e.g. 1500 Hz) to the total energy. Spectral decrease averages the set of slopes between each frequency bin gain and the gain of the first frequency bin. This feature provides characterization of the tone quality (timbre) of the analyzed speech.

Soft phonation index (SPI) may be used to assess laryngeal dysfunction, and abnormal vocal fold adduction which are associated with OSA. It is computed as the ratio of the energy in a low frequency band (70-1600 Hz) to the energy in a higher frequency band (1600-4500 Hz). Higher values of SPI may correlate with incomplete vocal fold adduction and are indicator of breathiness in speech.

Harmonic-to-noise ratio (HNR) assists in assessing the amount of turbulent noise energy added to the signal during phonation. Such turbulence is commonly caused by inadequate of incomplete vocal fold adduction. It also allows the quantification of speech hoarseness, which was associated with OSA. A procedure for computing HNR is detailed in the document Yumoto, E., W. J. Gould and T. Baer (1982). "Harmonics-to-noise ratio as an index of the degree of hoarseness." The journal of the Acoustical Society of America 71(6): 1544-1550.

Jitter measures the regularity of pitch periods, and it is represented as the average absolute difference between two consecutive periods, divided by the average period $$Jitter = \frac{\frac{1}{N-1}\sum_{i=2}^{N} |T_i - T_{i-1}|}{\frac{1}{N}\sum_{i=1}^{N} T_i},$$

where $T_i$ is the $i^{th}$ period duration (in seconds) of the analyzed segment, comprised of N periods.

Difference of differences of periods (DDP) Jitter quantifies the absolute difference of differences between cycles, divided by the average period, as $$JitterDDP = \frac{\frac{1}{N-2}\sum_{i=2}^{N-1} |T_{i+1} - T_i - (T_i - T_{i-1})|}{\frac{1}{N}\sum_{i=1}^{N} T_i}.$$

Shimmer is defined as the average absolute difference between the amplitudes of consecutive periods divided by the average amplitude $$Shimmer = \frac{\frac{1}{N-1}\sum_{i=2}^{N} |A_i - A_{i-1}|}{\frac{1}{N}\sum_{i=1}^{N} A_i},$$

where $A_i$ is the peak-to-peak amplitude of the $i^{th}$ period.

Amplitude perturbation quotient (APQ) is the average absolute difference between the amplitude of a period and the average of amplitudes of its neighbors, divided by the average amplitude. Specifically, APQ3 is the three-point APQ, computed as $$APQ3 = \frac{\frac{1}{N-1}\sum_{i=2}^{N} \left|A_i - \left(\frac{1}{3}\sum_{n=i-1}^{i+1} A_n\right)\right|}{\frac{1}{N}\sum_{i=1}^{N} A_i}.$$

Dynamic features represent a discrete time derivative (Delta, or Δ) of the frame-level static features. They are generally formulated as $$\Delta f[k] = \frac{\sum_{i=-T}^{T} w_i f[k+i]}{N[w]},$$

where $\Delta f[k]$ denotes the feature f at the $k^{th}$ time frame, $w_i$ is the $i^{th}$ weight and $N[w]$ is a normalization function of the weights.

Itakura distance measure is used to quantify the distortion between two LP representations (achieved through AR analysis). For a reference segment $\{x[n]\}$ with AR model coefficients $a_x$, there may be an input segment $\{y[n]\}$. The AR mean squared prediction error (MSE) of the reference pattern will be $E_{x,x} = a_x^T R_x a_x$, where $R_x$ is the autocorrelation matrix of the sequence $\{x[n]\}$. Similarly, mean squared prediction error of the input pattern $\{y[n]\}$, through the AR model estimated using $\{x[n]\}$, will be $E_{x,y} = a_y^T R_x a_y$. Finally, Itakura distance is formulated as follows:

$$d(x, y) = \log\left(\frac{E_{x,y}}{E_{x,x}}\right) = \log\left(\frac{a_y^T R_x a_y}{a_x^T R_x a_x}\right).$$

As the mean square prediction error of the input segment is close to this of the reference segment, the distance goes smaller.

In one embodiment, the STFs may be used to calculate a probability density function in multidimensional feature space, e.g. by multivariate distributions, such as a Gaussian mixture model (GMM).

A Gaussian mixture density is a weighted sum of M component densities, as given by the following equation $$p(o|\lambda) = \sum_{i=1}^{M} c_i b_i(o)$$

where o is a D-dimensional random observation vector, $b_i(o)$, $i=1, \ldots, M$ are the component densities, and $c_i$, $i=1, \ldots, M$ are the mixture weights. Each component density is a D-variate Gaussian function of the form $$b_i(o) = \frac{1}{(2\pi)^{D/2} |\Sigma_i|^{1/2}} \exp\left\{-\frac{1}{2}(o - \mu_i)^T \Sigma_i^{-1} (o - \mu_i)\right\}$$

with mean $\mu_i$ and covariance matrix $\Sigma_i$. The mixture weights have to satisfy the constraint $\Sigma_{i=1}^{M} c_i = 1$. The complete Gaussian mixture density is parameterized by the mean vector, the covariance matrix and the mixture weight from all component densities. These parameters are collectively represented by $\lambda = \{c_i, \mu_i, \Sigma_i\}$; $i=1, \ldots, M$. The covariance matrices $\Sigma_i$ may often be restricted to be diagonal. In the training process, the maximum likelihood (ML) procedure is adopted to estimate model parameters, by maximizing the likelihood of GMM given the training data. For a sequence of T training vectors $O = \{o_1, \ldots, o_T\}$, the GMM likelihood can be written as (assuming observations independence)

$$p(O|\lambda) = \sum_{t=1}^{T} p(o_t|\lambda).$$

The ML parameter estimates are obtained iteratively using the expectation-maximization (EM) algorithm. At each iteration, the parameter update formulas are as below, which guarantee a monotonic increase in the likelihood value. Mixture weight update may be given as $$\hat{c}_i = \frac{1}{T}\sum_{t=1}^{T} p(i|o_t, \lambda).$$

Mean vector update may be given as $$\hat{\mu}_i = \frac{\sum_{t=1}^{T} p(i|o_t, \lambda) o_t}{\sum_{t=1}^{T} p(i|o_t, \lambda)}.$$

Covariance matrix update may be given as $$\hat{\Sigma}_i = \frac{\sum_{t=1}^{T} p(i|o_t, \lambda)(o_t - \hat{\mu}_i)(o_t - \hat{\mu}_i)^T}{\sum_{t=1}^{T} p(i|o_t, \lambda)}.$$

The a posteriori for the ith mixture may be given by $$p(i|o_t, \lambda) = \frac{c_i b_i(o_t)}{\sum_{k=1}^{M} c_k b_k(o_t)}$$

Preferably, a plurality of STF sets obtained from the subject's phonogram may be used to calculate the probability density function. Additionally, a GMM universal background model (UBM) may be provided fitted with the same model order and dimensions to generate a vector to account for subject-independent statistics. The UBM vector may be calculated separately for male and female speakers. The UBM vector may be calculated from a database of healthy subjects. The GMM-UBM vector may then be modified with the subject's time frames' STF, to obtain a subject-specific distribution model vector, using a maximum a posteriori approach, as described, e.g. in the document Reynolds, D. A., T. F. Quatieri and R. B. Dunn (2000). "Speaker verification using adapted Gaussian mixture models." Digital signal processing 10(1): 19-41. The means of the components of the adapted mixture model may be concatenated to create a super vector. The super vector may also comprise anthropometric data, e.g. BMI, age, gender, or any combination thereof. In further embodiments, a computing systems (e.g. machine learning models, classifiers, super vector machine regression (SVR) model) may be used to calculate an estimation of AHI derived from STF (from the super vector), i.e. $AHI_{ST}$. Additionally or alternatively, further suitable computing systems (e.g. machine learning models, classifiers) may be used to obtain the subject-specific features distribution, and optionally being further processed into a super vector as disclosed above; the computing systems may be exemplified by but not limited to Hidden Markov Model, and Artificial Neural Network.

While the sets of STF, their respective GMM orders and dimensions may be particularly suitable in some populations, other STF may be suitable in particular population speaking any particular language. The STF in a particular population may be selected using sequential forward selection (SFS) algorithm. The selection algorithm may be used to reduce the complexity of the system the amount of computed parameters, by reducing the dimension of the feature vector, as described, e.g. in the document Pudil Pavel, Jana Novovičová, and Josef Kittler. "Floating search methods in feature selection." Pattern recognition letters 15.11 (1994): 1119-1125). GMM may be computed using the diagnostic results from PSG, and orders and dimensions of the adapted GMM may be optimized using the same SFS approach. The adapted GMM may be then cross-validated using the data from PSG, and further modified to reach the highest accuracy.

In one embodiment, a set of features comprises long term features (LTF). The LTF are extracted by framing an appropriate segment of phonogram signal with long frames. The long frames may have a duration of longer than about 30 ms, e.g. 128 to 512 ms, or between 240 and 270 ms, e.g. 256 ms, with a frame shift of between 20 and 80 ms, or between 60 and 70 ms, e.g. 64 ms. Sometimes, before extracting the LTF, a pre-processing may be applied, the pre-processing comprising detecting voice activity, and applying an auto-correlation function, for each of the long-term frames. These steps may assist in determination whether an uttered phoneme of the long-term frame is voiced or unvoiced. In one embodiment, for each of voiced and unvoiced frames features may be extracted, the features include the power of signal, the median frequency, and the central spheroid (i.e. mean frequency). The plurality of power features may then be used to calculate a feature $PR_{vuv}$, by taking a $10^{th}$ logarithm from the ratio of the average of the plurality of power values of voiced frames and the average of the plurality of power values of the unvoiced frames. For the plurality of median frequency values and the plurality of central spheroid values the means and variances of the voiced and unvoiced frames may be calculated.

In a further embodiment, it has been found that LTF suitable for the OSA evaluation include a set of features. In one embodiment, the LTF set suitable for OSA evaluation in male speakers comprises an arithmetic mean of a first time derivative of spectro-temporal energy $\Delta\Phi^{(3)}$, an inter-quantile range of second time derivative of linear prediction cepstral coefficients $\Delta\Delta LPCC_1^{(1)}$, a variance of $LPCC_3^{(3)}$, an inter-quantile range of $LPCC_3^{(3)}$, and an inter-quantile range of $LPCC_3^{(1)}$. In a further embodiment, the LTF set suitable for OSA evaluation in female speakers comprises a variance of $LPCC_4^{(3)}$, a variance of $LPCC_4^{(1)}$, variance of $\Phi^{(3)}$, and an arithmetic mean of $LPCC_1^{(2)}$. Without being bound by a theory it is believed that the inclusion of $\Phi^{(3)}$ might reflect the more monotonic speech among OSA patients, apparently correlating negatively with AHI, may result from muscle fatigue and fatigue of the patient in general.

In one embodiment, a set of LTF, and optionally anthropometric data, e.g. BMI, age, gender, or any combination thereof, may be used to calculate an estimate of the LTF-based AHI ($AHI_{LT}$), using computing systems (e.g. machine learning models, classifiers) e.g. regression tree ensemble approach, optimized to minimize mean square error versus polysomnogram-derived AHI using least-square boosting.

Given a set of N training samples $D=\{(x_1, y_1), \ldots, (x_N, y_N)\}$, the goal in gradient boosting machines (GBM) is to obtain an approximation $\hat{F}(x)$, of the function $F(x)$ mapping x to y, that minimizes the expected value of a certain loss function $L(y, F(x))$ over the joint distribution of all $(x, y)$ values.

A member of a parametrized class $F(x)$ to be of functions may be restricted, $$F(x, \{\beta_m, a_m\}_1^M) = \sum_{m=1}^{M} \beta_m h(x; a_m),$$

where $h(x; a)$ is a generic simple parametrized function of the input variables x, characterized by a set of parameters $a=\{a_1, a_2, \ldots\}$. In least-square boosting, the functions $h(x; a_m)$ may be small regression trees. For a regression tree the parameters $a_m$ are the splitting variables, split locations and the terminal node means of the individual trees. Moreover, the loss function is defined to be $L(y, F(x))=(y-F(x))^2/2$. The boosting starts with a naive approximation of the dependent variable, then applying stagewise approach, iteratively fits the residuals of the approximation obtained on the previous iteration. The mixing coefficients of the ensemble components $\beta_m$, as well as the parameters of each learner on each stage $a_m$, are optimized using steepest-descent method. In one embodiment, an algorithm may be used as follows:
$F_0(x)=\bar{y}$//initialize approximation
For m=1 to M do: //for M learning cycles $$\tilde{y}_i = y_i - F_{m-1}(x_i), i = 1, \ldots, N$$

//set target as previous approximation residual
//optimize parameters of current learner $$(\rho_m, a_m) = \operatorname{argmin}_{a,\rho} \sum_{i=1}^{N} [\tilde{y}_i - \rho h(x_i; a)]^2$$

$$F_m(x) = F_{m-1}(x) + \rho_m h(x; a_m)$$

end

Preferably, the plurality of LTF sets may be used to calculate $AHI_{LT}$ directly, using the regression tree ensemble approach, as described herein.

While the sets of LTF, their respective computing system parameters, e.g. regression tree ensemble parameters, demonstrated above may be particularly suitable in some populations, other LTF may be suitable in a particular population speaking any particular language. The LTF in a particular population may be selected using sequential floating forward selection (SFFS) algorithm, as described, e.g. in the document Ferri, F., P. Pudil, M. Hatef and J. Kittler (1994). "Comparative study of techniques for large-scale feature selection." Pattern Recognition in Practice IV: 403-413, and further cross-validates using the diagnostic results from PSG, and optionally further modified to reach the highest correlation.

In one embodiment, a set of features may also comprise sustained-vowel features (SVF). The SVF are extracted by framing the appropriate segment of phonogram with short frames, as described herein. The frames may be preprocessed, e.g. by framing the utterances to 30 ms frames with high rate of overlap (90%) between adjacent frames, windowing using a rectangular or Hamming window function, and performing pre-emphasis filtering. In one embodiment, features may be extracted, the features include a spectral flatness measure. The spectral flatness measure may be calculated as geometric mean of power spectral density estimate for the plurality of the frames divided by their arithmetic mean. Without being bound by a theory it is believed that spectral flatness may be associated with hypernasal speech, wherein abnormal nasalization may be associated with OSA. Further features may be extracted from the pluralities of time frames derived from the sustained-vowel segment. These features may be processed to derive a statistical estimate of their distribution, e.g. arithmetic or geometric mean, standard deviation, kurtosis, skewness, extrema, and specific quantiles.

In a further embodiment, it has been found that SVF suitable for the OSA evaluation include a set of features. In one embodiment, the SVF set suitable for OSA evaluation in male speakers comprises a "u:" phoneme arithmetic mean of SPI, an "e" phoneme geometric mean of spectral flatness, a "u:" phoneme zero crossing rate of $\Delta MFCC_1$, an "ɒ" phoneme zero crossing rate of $\Delta MFCC_2$, and an "ɒ" phoneme inter-quartile range of $\Delta MFCC_4$. In a further embodiment, the SVF set suitable for OSA evaluation in female speakers comprises an "ɒ" phoneme skewness of $MFCC_5$, an "a:" phoneme maximum of spectral flatness, an "e" phoneme arithmetic mean of APQ3, an "a:" phoneme quadratic mean of shimmer, and an "i" phoneme second quartile of $MFCC_{12}$. The skewness was calculated using non-adjusted Fisher-Pearson coefficient of skewness, according to the formula $$s_1 = \frac{\frac{1}{n}\sum_{i=1}^{n}(x_i - \bar{x})^3}{\left(\sqrt{\frac{1}{n}\sum_{i=1}^{n}(x_i - \bar{x})^2}\right)^3}$$

In one embodiment, a set of SVF and optionally anthropometric data, e.g. BMI, age, gender, or any combination thereof, may be used to calculate an estimate of the SVF-based AHI ($AHI_{SV}$), using e.g. a regression tree ensemble approach as described above. Preferably, the plurality of SVF sets may be used to calculate $AHI_{SV}$ directly, using the regression tree ensemble approach, as described herein.

While the sets of SVF, their respective regression tree ensemble parameters demonstrated above may be particularly suitable in some populations, other SVF may be suitable in a particular population speaking any particular language, particularly with other phonemes. The SVF in a particular population may be selected using sequential floating forward selection (SFFS) algorithm, as described above, and further cross-validates using the diagnostic results from PSG, and optionally further modified to reach the highest correlation.

In further embodiments, the method of estimating AHI from the three systems comprises fusing of the estimated AHI values across the three subsystems. The fusing may be performed using a linear regression model, e.g. with elastic net regularization. For the elastic net regularization, the independent variables may be the three AHI estimation results, and the desired response (dependent variable) is the diagnosed AHI. The regularization parameter may be chosen using K-fold cross validation (K=10) on the design dataset, as the one which yields minimum mean square error between the prediction of the model and the desired response. Alternatively or additionally, the fusing of the scores may be performed by any suitable regression between the estimations and the PSG scores of a tested subject. Further alternatively or additionally, the scores may be averaged and fitted into a linear or non-linear regression, thus providing an equation, e.g. a quadratic equation, to estimate the fused score of AHI.

In a further aspect of the present invention, the estimation of the AHI may be performed by evaluating a plurality, e.g. at least a pair, of phonograms of the same subject, in a sequential manner. Preferably, the phonograms may be obtained under varying speaking conditions. In one embodiment, the varying speaking condition may include a posture, e.g. the first phonogram may be obtained in an upright or a sitting position and a consecutive in a supine or prone position. In a further embodiment, the varying speaking condition may include a reference to the somnal state, e.g. a first phonogram may be obtained in a defined posture hora somnie (i.e. before bedtime), and a a consecutive phonogram may be obtained postsomnially (i.e. right after the awakening) in the same or different posture, preferably a lying posture.

In some embodiments, the varying speaking conditions include posture change. In these embodiments, the preferred speaking protocol is sustained vowel protocol. This protocol may be used to provide the severity of the OSA by estimating the AHI, and may also be used to classify a subject into an OSA or a healthy category. For the purpose of to providing the severity of the OSA by estimating the AHI, the same steps as described above for sustained vowels segment of the speaking protocol may be performed, e.g. preprocessing, etc. The obtained phonogram may then be processed to extract features. For a male subject, the features may include any one of the features a phoneme "a" mean of $MFCC_3$, a phoneme "ɒ" variance of second time derivative of $MFCC_1$, a mean of shimmer, and a mean of spectral crest. For a female speaker, the features may include a phoneme "a" variance of $MFCC_6$, a phoneme "ɒ" mean of a first time derivative of $MFCC_2$, and a phoneme "u" mean of $MFCC_6$.

In some further embodiments, the varying speaking conditions include posture change, and may be used to provide the severity of the OSA by estimating the AHI. For the purpose of AHI estimation, the same steps as described above for sustained vowels segment of the speaking protocol may be performed, e.g. preprocessing, etc. The obtained phonogram may then be processed to extract features. For a male subject, the features may include any one of the features a phoneme "a" variance of jitter DDP, a phoneme "i" mean of second time derivative of $MFCC_4$, a phoneme "u" mean of second time derivative of $MFCC_1$, and a phoneme "e" mean of first time derivative of $MFCC_{12}$. For a female speaker, the features may include a phoneme "e" mean of $MFCC_6$, and a phoneme "i" mean of a first time derivative of $MFCC_4$.

Without being bound by a theory it is believed that the inclusion of features from high tongue vowels (e.g. "i" and "e") and of central-back tongue vowels (e.g. "a" and "u") might result from the clinical features which are associated with OSA, namely relatively enlarged tongue and inferiorly placed hyoid bone. Moreover, for the male subjects, one time-domain feature (i.e. the variance of jitter DDP) may be used for speech-based assessment of vocal cord adduction (associated with OSA), and may provide information concerning the regularity in voice production. The MFCC features provide perceptual description of the vocal tract shape, and its dynamic behavior, which may be presented differently in OSA patients. The shimmer measure is used to assess phonation disorders, which are associated with OSA.

Spectral crest provides quantification of the spectral energy distribution. It is also believed that the structural differences in the upper respiratory tract among OSA patients may be reflected in the spectral energy distribution.

In some preferred embodiments, the features may comprise a linear combination of features extracted from the first phonogram, e.g. obtained in an upright position, and at least one consecutive phonogram, e.g. obtained in a lying position. Alternatively or additionally, the features may comprise a difference between the first and at least one consecutive phonogram, or between any features extracted from the said first and at least one consecutive phonogram.

In some further embodiments, the varying speaking conditions include somnal state, and may be used to provide the severity of the OSA by estimating the AHI. The obtained phonogram may then be processed to extract features. For any subject, the features may include any one of the features a phoneme "u" the difference between the means of a first time derivative of $MFCC_{12}$, and a phoneme "i" the difference between the means of jitter DDP. For both of the features the difference may computed between at least two utterances of the phoneme, wherein a first being uttered hora somnie, and the second being uttered immediately postsomnially, i.e. with awakening. In further preferred embodiments, the both utterances may be obtained in supine position.

The features may be processed to furnish the classification, or the estimate of AHI in the subject. The processing may include a regression tree ensemble, e.g. by least square boosting. The ensemble may be prevalidated using a K-fold cross-validation scheme, as described above, wherein K may be equal to an integer between 7 and 13, e.g. 10, may be used. Alternatively, the features may be fed into a regression model, obtained by fitting the values to furnish the target AHI.

Referring now to FIG. 1, schematically showing a flow chart to train the system to determine the severity of OSA in a wake subject. In the training process the preformed models used in the computing systems of the AHI determination stage, are determined. A recording device is used to obtain a plurality of phonograms of OSA and healthy subjects, comprising the database 10, denoted schematically as DB, and a plurality of phonograms of healthy unrelated subjects, comprising the universal background database 20, denoted as UBM-DB. The database comprises the phonograms associated with PSG scores of the subjects and their respective anthropometric data. The phonograms of the database 10 may then be divided into two groups, a design database 100 and a validation database 200, denoted DesDB and ValDB, respectively, using a computing system adapted to perform this and following steps. The phonograms of the databases 20, 100, and 200 may then be preprocessed and segmented into time frames, the steps designated as 22, 120, and 220, respectively, to furnish a database comprising a plurality of preprocessed and segmented phonograms. Further steps may be performed in parallel for each phonogram of a database, or may be performed consecutively.

The phonograms of the database 120 may be framed and further processed to extract three sets of features for each phonogram signal, namely, STF, LTF and SVF. The framing for short frames and extracting of STF is demonstrated as a step 140 and denoted STFE, the framing for long frames and extracting of LTF is demonstrated as a step 160 and denoted LTFE, and framing for short or long frames and extracting of SVF is demonstrated as step 180, and denoted as SVFE. The STF from the step 140 are fitted to a classifier, e.g. to a Gaussian mixture model, using the AHI obtained by PSG, appended to each phonogram, demonstrated as step 144, denoted as STFM. The selected features and model order may then be transferred to the segmented phonograms of database 22, to obtain a speaker-independent probability density distribution of the selected features, designated as step 24, denoted as UBMSTFE. The UBM components obtained from the step 24 may then be adapted to the individual speaker's specific feature vectors distribution, designated as step 26 and denoted UBMMx, e.g. by using a maximum a-posteriori approach. The mean vectors of the mixture components of the adapted model obtained in the step 26 may then be concatenated into a super-vector in a step 28, by optionally appending anthropometric data of the speaker (not shown), and extracting an i-vector, denoted as "i-Vec". The set of extracted i-vectors is then used with the AHI values in training a regression trees ensemble, designated as 148, and denoted as RTES, to furnish a fitted STF computing system model. The model may then be validated by providing i-vectors from pre-processed phonograms obtained from validation database in step 220, and feeding them into the estimation computing system model obtained from the step 148, in a step 244, denoted fSTFM, to furnish an estimate of $AHI_{ST}$.

The LTF extracted in the step 160, may be selected using a sequential floating forward selection (SFFS) algorithm, and fitted to a regression trees ensemble classifier using the AHI obtained by PSG, appended to each phonogram, in the LTF modeling step, designated 164 and denoted LTFM, to furnish a selected LTF subset. Anthropometric data may optionally be appended to the selected LTF subset (not shown), and further regression trees ensemble may be trained in the step 168, designated RTEL, to furnish a fitted LTF model, shown in a step 246, and designated accordingly fLTFM.

Similarly, The SVF extracted in the step 180, may be selected using a sequential floating forward selection (SFFS) algorithm, and fitted to a regression trees ensemble classifier using the AHI obtained by PSG, appended to each phonogram, in the SVF modeling step, designated 184 and denoted SVFM, to furnish a selected SVF subset. Anthropometric data may optionally be appended to the selected SVF subset (not shown), and further regression trees ensemble may be trained in the step 188, designated RTEV, to furnish a fitted SVF model, shown in a step 248, and designated accordingly fSVFM.

Additionally, the steps 148, 168, and 188 may provide an estimate of $AHI_{ST}$, $AHI_{LT}$, and $AHI_{SV}$, respectively, for a fusion model step 190, which may be used as a reference in the validation phase at score fusion step 290, designated "ScFus".

Figure 2:
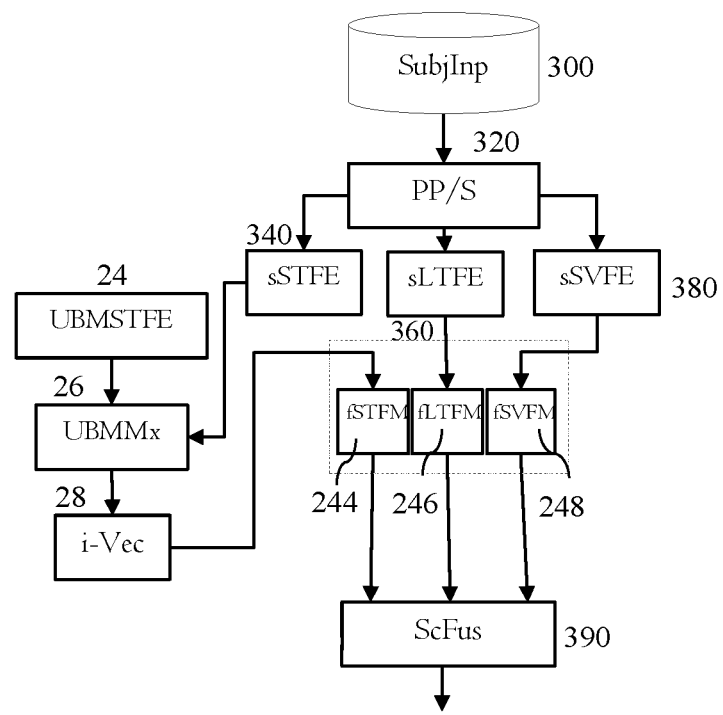
FIG. 2 schematically demonstrates a flow chart for determination of an estimate of AHI of a wake subject according to a one embodiment of the invention.

Referring now to FIG. 2, schematically showing a flow chart of the system operating to determine the severity of OSA in a wake subject. A wake subject's phonogram 300 is pre-processed and segmented in the step 320, denoted as PP/S, and selected STF set, selected LTF set and selected SVF set are extracted in the steps 340, 360, and 380, respectively. The selected set of STF from the step 340 may be fitted to a classifier, e.g. Gaussian mixture model. A set of selected STF may also be provided as the UBM components from the universal background model, e.g. as described in the FIG. 1, as step 24, and may further be adapted to the individual speaker's specific feature vectors distribution, designated as step 26 and denoted UBMMx, e.g. by using a maximum a-posteriori approach. The mean vectors of the mixture components of the adapted model obtained in the step 26 may then be concatenated into a super-vector in a step 28, by optionally appending anthropometric data of the speaker (not shown), and extracting an i-vector, denoted as "i-Vec". The set of extracted i-vectors is then used in the fitted STF model in step 244, designated fSTFM, to provide an estimate of $AHI_{ST}$. The selected set of LTF from the step 360 may be used in the fitted LTF model in step 246, designated fLTFM, to provide an estimate of $AHI_{LT}$. The selected set of SVF from the step 380 may be used in the fitted LTF model in step 248, designated fSVFM, to provide an estimate of $AHI_{SV}$.

The estimates $AHI_{ST}$, $AHI_{LT}$, and $AHI_{SV}$, obtained in the steps 244, 246, and 248 may be provided as an input for a fusion model step 390, designated "ScFus".

Whereas the invention has been generally described in the foregoing embodiments thereof, it may be better understood in view of the examples below, which do not limit the disclosure in any respect.

EXAMPLES

OSA Severity Estimation Through a Speaking Protocol

The database for the presented study is comprised of 333 speech signals (214 men and 119 women). Most of the speech signals (314; 205 of men and 109 of women) were recorded from subjects who were referred to the Sleep-Wake Unit of Soroka University Medical Center for an overnight sleep study; in order to evaluate sleep-disordered breathing. Out of the 314 subjects, 202 subjects (132 men and 70 women) were diagnosed in lab through a PSG study, and the sleep of the remaining 112 subjects (73 men and 39 women) was evaluated at home using a type IV device such as "watchPAT-100" or "watchPAT-200" (by Itamar Medical Ltd.). The remaining 19 speakers (9 men and 10 women) of the entire 349 speakers set, were students in Ben-Gurion University of the Negev who participated voluntarily in the research. The motivation of incorporating subjects who are not prior suspected to suffer from OSA, comes from the ambition to balance the skewness of the previous setup database, which included much more OSA patients than non-OSA patients.

Each subject was recorded using a digital audio recorder (handy recorder "H4" by "ZOOM"), while reading a one-minute text protocol in Hebrew that was designed to emphasize certain characteristics of speech. The digital signals were recorded using a sampling rate of 44.1 kHz (16 bits/sample), then downsampled to 16 kHz. The speech protocol included pronunciation of sustained vowels; sentences which will allow examination of the dynamic properties of speech; yes no questions; and a list of isolated words. Immediately after speech recording, each subject underwent an overnight sleep study, which was later scored by sleep experts from the medical staff of the sleep clinic, to yield the AHI value and OSA diagnosis. The Institutional Review Committee of the Soroka University Medical Center approved the study; informed consent was obtained from all subjects.

Apart from the gender-based division of the speakers, in order to avoid overfitting, the database was divided into two separate datasets: design and validation. Due to the fact that PSG is the gold-standard for OSA diagnosis and evaluation, the design datasets (for both genders) are comprised exclusively from speakers who underwent PSG study. The division of the speakers to design and validation datasets was performed in a way which preserves statistical similarity across AHI, BMI and age.

The speaking protocol included the following instructions:
Protocol transcription in English:
Read the following syllables out load, 3 seconds for each syllable:
/a/,
/i/,
/u/,
/e/,
/o/,
/m/
/n/
Read the following sentences naturally:
Hashulhan hu agol
Hamakor haiahid leieda hu hanisayon
Ota hageveret beshinuy aderet
Efshar lehovil et hasus labe'er aval lo lehahriach oto lishtot
Hatapuah lo nofel rahok meaetz
Lo konim hatul basak
Amarti lahem lavo
Malon hamisha cohavim im nof layam lameshulash yesh shalosh pinot.
Read the following questions naturally:
Amarta lahem lavo?
Halimon hamotz?
Haim zeho sus pony?
Atem shatim bekanu?
Saba ba?
Haim ze ma sheata rotze?
Kasha lech linshom?
rotze lishon?
Read the following sentences naturally:
Leimma korim mama
Hamesh shmone shalosh
Leabba korim baba
Arba ehad shesh
Lesavta korim nana
Ehad shmone hamesh
Lesaba korim dada
arba shesh shalosh
Read the following words
Ma Lo
Fa Ze
Hu Lo
Do Ken
Fe Mi For all the subsystems, pre-processing stages included DC removal and energy normalization. The analog speech signal was sampled and quantized in order to provide a digital signal, suitable for digital processing. The DC component generated by the recording device and its inner amplifiers, was subtracted from the analyzed signal. In order to compensate for different recording conditions, such as varying distances between the speakers and the recording device, which affects the gain of the resulting digitized signal, the amplitude level of the signal was normalized by an 80% percentile of the computed energy measures along the entire recording.

The sustained vowels portion of the phonogram was segmented manually. The segmented utterances were framed to 30 ms frames with high rate of overlap (90%) between adjacent frames, to ensure the presence of sufficient amount of frames for statistical description. The spectral analysis included pre-emphasis filtering, and windowing using Hamming window function. Each segmented phoneme went through the extraction of 53 frame-level spectral and temporal features. These descriptors include 13 Thomson Multitaper mel-frequency cepstral coefficients (MFCC), as well as the first and second time derivatives, to capture the cepstral characteristic of the uttered phoneme and its dynamic properties. Spectral behavior was measured using harmonic-to-noise ratio (HNR) to capture voice quality, and additional spectral descriptors. Time-domain behavior was measured using Jitter, Jitter DDP, Shimmer, and amplitude perturbation quotient (APQ), to assess regularity in voice emission.

The extraction yielded length-varying time sequences of features, which might reflect the time track of the acoustic descriptors throughout the utterance. In order to allow the description of the uttered phoneme in the perspective of the extracted features, in a manner which preserves similar quantity of measures for each instance, functionals were applied on each feature sequence. These functionals are applied in order to quantify the progression in time of each sequence, as well as its statistical properties. The application of the functionals on each feature sequence of each phoneme, generated a fixed-length feature vector for every patient. The components of the resulting vector are denoted as sustained vowels features (SVF). These are summarized in the Table 1 below.

Long-term subsystem processes the continuous part of the speech signal, in order to capture speech patterns presenting a more "natural" form of pronunciation. The pre-processed speech signals were framed to relatively long frames (of 256 ms), with a time-shift of 64 ms and a Hamming window. Silence removal was performed using a voice activity detector (VAD) based on abovementioned publication Sohn 1999.

TABLE 1

| Frame-level descriptors | Feature sequence functionals |
|---|---|
| Multitaper MFCC + $\Delta$ + $\Delta\Delta$ (13 × 3) | Arithmetic mean |
| Spectral centroid | Quadratic mean (RMS) |
| Spectral flatness measure (SFM) | Variance |
| Spectral crest factor | Skewness |
| Spectral skewness | Kurtosis |
| Spectral kurtosis | Contour centroid |
| Spectral entropy | Zero crossing rate (ZCR) |
| Spectral brightness | Rise-time quotient |
| Spectral decrease | Minimum value |
| Soft phonation index (SPI) | Maximum value |
| Harmonic-to-noise ratio (HNR) | Inter-quantile range (IQR) |
| Jitter | $1^{st}$ quartile |
| Jitter DDP | $2^{nd}$ quartile |
| Shimmer | $3^{rd}$ quartile |
| 3-point Amplitude perturbation quotient (APQ3) | |

The spectro-temporal representation was computed using gammatone filterbank comprised of 19 channels, and a modulation filterbank comprised of 5 channels, according to the publication Wu, S., T. H. Falk and W.-Y. Chan (2009). Automatic recognition of speech emotion using long-term spectro-temporal features. 2009 16th International Conference on Digital Signal Processing, IEEE. This approach was applied in the long-term subsystem in order to obtain the modulated sub-band energy measures, denoted as $\Phi_k^{(m)}$. In addition, the outputs of the modulation channels went through a low-order LP analysis (p=5) to obtain linear prediction cepstral coefficients (LPCC). Hence, from each frame were extracted 5 modulated sub-band energy measures, and 30 LPCCs (six for every modulation channel), concluding 35 frame-level descriptors, in addition to their first and second order time derivatives.

As in the sustained-vowels subsystem, the continuous speech recordings vary in length across the different speakers. Thus, in order to quantify the contour (trajectory) of the frame-level descriptors, the mean, variance, and IQR were calculated, and concatenated to form a fixed length long-term features (LTF) vector. The long-term frame level features and their statistic measures are listed in Table 2 below.

TABLE 2

| Long-term frame level features | Statistic measures |
|---|---|
| Modulated sub-band energies: $\Phi^{(m)}$ + $\Delta$ + $\Delta\Delta$ $1 \leq m \leq 5$ | Arithmetic mean |
| Modulation channels linear prediction cepstral coefficients (LPCC): $LPCC_i^{(m)}$ + $\Delta$ + $\Delta\Delta$, $1 \leq i \leq 6$, $1 \leq m \leq 5$ | Variance |
| | Inter-quantile range (IQR) |

Short-term subsystem performs analysis of the continuous part of the speech signal solely. Apart from DC removal, energy normalization, pre-emphasis filtering, and voice activity detection, the signals were framed using Hamming windows of 30 msec duration, with an overlap rate of 50% between adjacent frames.

The universal background model (UBM) database went through the exact same stages of pre-processing and feature extraction as elaborated below. Features were extracted as follows from each time frame: 18 Thomson multitaper MFCC, as well as their first and second time derivatives, 18 SWCE representation coefficients, 12 GFCC, and 13 MHEC. The features extracted are summarized in the Table 3 below.

TABLE 3

| Short-term features | Quantity | Symbol |
|---|---|---|
| Thomson multitaper mel-frequency cepstral coefficients (MFCC) | 18 | $c_1$-$c_{18}$ |
| $\Delta$ Thomson multitaper MFCC | 18 | $\Delta c_1$-$\Delta c_{18}$ |
| $\Delta\Delta$ Thomson multitaper MFCC | 18 | $\Delta\Delta c_1$-$\Delta\Delta c_{18}$ |
| Sine-wave cepstrum estimator (SWCE) | 18 | $SWCE_1$-$SWCE_{18}$ |
| Gammatone-frequency cepstral coefficients (GFCC) | 12 | $GFCC_1$-$GFCC_{12}$ |
| Mean Hilbert envelope coefficients (MHEC) | 13 | $MHEC_1$-$MHEC_{13}$ |

Each of the developed subsystems were embodied by a prediction model for OSA severity estimation, in terms of AHI. These models were estimated using the design dataset, and validated on the validation dataset, according to the hold-out method. After acquiring the estimations of the three subsystems, a fusion procedure was performed in order to leverage the performance of the whole system. Prior to the estimation of the final models, a procedure for selecting the most informative features for the problem in hand was executed, in order to reduce the dimension of the problem and minimize the risk of over-fitting. Model estimation and validation procedure were similar in both, the sustained vowels subsystem and the long-term subsystem.

In the sustained vowels subsystem and the long-term subsystem, the procedure of model estimation included feature and model selection. For performing the selection the sequential floating forward selection (SFFS) algorithm was used, with a criterion which is dependent of the learning paradigm performance. Simultaneously to the selection of feature subset, the order of the model was also selected in order to optimize the performance of the model. The learning paradigm for these subsystems was an ensemble of regression trees, in which the order of the model is represented by the amount of learning cycles.

Pearson correlation coefficient (marked as ρ) between the target value (diagnosed AHI) and the predicted AHI according to the computed model was used. In order to allow a more generalized selection, which does not fit only a certain portion of the database, for each subset selection $X_k$ (where $X_k \in X_{All}$, the entire feature set), Monte-Carlo cross-validation (MCCV) procedure was performed to evaluate the performance criteria. For this matter, the design dataset (consisting N data points) was split P times into two subsets $S_{train}^{(p)}$ and $S_{valid}^{(p)}$, by sampling (without replacement), $n_{train}$ data points (where, p=1, . . . , P, and $n_{train}$ is a fixed fraction of N). For each split p, an ensemble of regression trees $F^{(p)}(x)$ was trained according to the dataset $S_{train}^{(p)}$, using least-squares boosting technique. Then, the correlation coefficient between the predictions of $F^{(p)}(x)$ for the current test dataset $S_{valid}^{(p)}$, and the target values for this dataset was computed. Finally, the average correlation coefficients computed across all the P splits served as the performance measure for the examined feature subset. The value P=30 was used, and $n_{train}$ resembles a fraction of 70% out of the N data points comprising the design dataset.

The final feature subset was comprised of the selected LTF/SVF (according to the procedure elaborated above), and of the age and the body-mass index (BMI) of each speaker. Using the formed feature subset, the final prediction model, in the form of a regression trees ensemble, was trained using the entire design dataset. The parameters of the model were estimated using gradient steepest-descent.

After the model parameters were estimated in the training phase, validation procedure was conducted in order to evaluate the performance of the system. When an unknown speaker was introduced to the system, the digital speech signal underwent identical pre-processing procedures to those embodied in each subsystem. The previously selected features. for each subsystem (SVF for the sustained vowels subsystem, and LTF for the long-term subsystem), are extracted and saved as feature vectors $x^{SVF}=[x_1^{SVF}, x_2^{SVF}, \ldots, x_N^{SVF}]$, and $x^{LTF}=[x_1^{LTF}, x_2^{LTF}, \ldots, x_K^{LTF}]$. For each subject from the validation dataset, the feature vectors $x^{SVF}$ and $x^{LTF}$ were fed into the estimated regression models $F_{SVF}(x^{SVF})$ and $F_{LTF}(x^{LTF})$, respectively, in order to yield the corresponding AHI estimates, $AHI_{SV}$ and $AHI_{LT}$, which serve as measures for OSA severity estimate.

The short-term subsystem was based on GMM-UBM feature space modeling, cascaded with the derivation of supervectors and subsequently the extraction of i-vectors. According to this approach, for a given utterance of a speaker, the GMM-UBM is adapted; subsequently, the D-dimensional mean vectors of the M-component adapted GMM are stacked into a MD-dimensional Gaussian supervector, which may serve as an input for a classification system (such as a support vector machine classifier). Later on, an i-vector was formulated. The formulation of the paradigm assumes a low-dimensional space, called total-variability (TV) subspace, according to which each acquired supervector, s, can be re-written as s=m+Tw, where m stands for the speaker-independent global representation, computed as the mean supervector of the UBM dataset. The TV matrix (also known as factor loading matrix), T, is a rectangular low rank matrix, computed using EM approach. The i-(identity) vector w, whose components are called total factors, is a random vector having a multivariate standard normal distribution N(0, I). The benefit of using i-vector modelling over adapted mean supervectors, is the projection of high-dimensional space into a low-dimensional subspace, where most of the speaker-specific variability is captured.

The subsystem includes the computation of a universal background mixture model (GMM-UBM) $\lambda^{UBM}$, composed of $M^{UBM}$ components. The UBM database was constructed from speech recordings of 74 men and 78 women (separate UBMs were trained for each gender). Speech recordings were acquired using the same recording device as the database of this study, while reading a different text protocol in Hebrew. The UBM speakers were not involved in any other aspect of this study. After training the UBM to achieve estimation of the speaker-independent probability density in the feature space, separately for each speaker (of the design dataset) the model was adapted for achieving the speaker-specific density estimation. The approach maximum a-posteriori (MAP) estimation was utilized for the adaptation of the UBM components mean vectors to the speaker specific feature vector distribution, achieving $\lambda^{adapted}$.

For each speaker the adapted model was used for forming a supervector, by stacking the mean vectors of the mixture components $\mu_i^{adapted}$, where $1 \leq i \leq M^{UBM}$. As in the long-term subsystem, and in the sustained vowels subsystem, and for the same considerations, two additional features were appended to each speaker's supervector: age and BMI. Finally, the supervector was formed as $x=[\mu_1^{adapted}, \mu_2^{adapted}, \ldots, \mu_{M^{UBM}}^{adapted}, Age, BMI]^T$. The elaborated procedure was used for the selection of feature subset (out of the short-term features set), and of the model order $M^{UBM}$.

For the short-term subsystem, the sequential forward selection (SFS) algorithm was applied for selecting the feature subset, in order to reduce computational expense (relative to SFFS). SFS was applied for different settings of $M^{UBM}$ in order to optimize the performance in terms of model order. For each setting of $M^{UBM}$ and for each examined feature subset, a set of supervectors was computed for the design dataset. The performance criterion of the examined subset was evaluated using MCCV. For each simulation p (out of P), a regression model was trained according to the supervectors of the partial design set $S_{train}^{(p)}$, and their desired response (AHI). The $p^{th}$ regression model was tested on the supervectors of $S_{valid}^{(p)}$, and the correlation coefficient between the prediction of the model and the AHI values of the dataset $S_{valid}^{(p)}$ was computed. Finally, the mean of the P correlation coefficients, acquired across the different MCCV splits, served as the performance criteria, according to which the selection was made.

After selecting the feature subset and the model order, and training the GMM-UBM, i-vector extraction was performed. This extraction is an outcome of a factor analysis, according to which each supervector can be formulated as s=m+Tw, where m stands for the speaker-independent global representation, computed as the mean supervector of the UBM dataset, and T is the rectangular low rank total-variability (TV) matrix, computed using EM algorithm, and w is the i-vector, whose components are called total factors. The total-variability dimension, controlled by the dimension of the matrix T, and determining the dimension of the extracted i-vectors, was also optimized using MCCV over the design dataset, in order to achieve maximal correlation between the predicted AHI, and the diagnosed AHI.

After setting the feature subset and the model order, and computing the TV matrix according to the UBM, i-vectors were extracted for the design dataset. The set of extracted i-vectors, and their corresponding AHI values, were used for the training of a regression ensemble $F_{STF}(x^{STF})$, using LS boost technique.

The performance of the short-term subsystem was finally evaluated using the validation dataset. Each speech signal underwent identical pre-processing procedures as those performed over the design dataset, and the selected features were extraction. Then, a supervector was formed using an adaptation of the computed UBM, and subsequently the computed TV matrix was utilized for the extraction of an i-vector $x^{STF}$. For each subject from the validation dataset, the resulting i-vector was fed into the estimation regression model $F_{STF}(x^{STF})$, in order to yield an AHI estimate $AHI_{ST}$.

In order the allow combination of the estimated AHI values across the three presented subsystems, a fusion procedure executed. The fusion embodies a linear regression model with elastic net regularization, where the independent variables are the three estimation results, and the desired response (dependent variable) is the diagnosed AHI.

Elastic net is a form of regularized regression, which suggests a compromise between ridge regression (which uses an L2 penalty) and Lasso regression (which uses an L1 penalty). The purpose of model regularization is to obtain smoother prediction models, with less tendency of overfitting to the data from which they are computed. Practically, the regularization is expressed through the cost function of the optimization problem in hand. If a regression model β (producing the prediction ŷ=Xβ), and a data set X, of N samples and p predictors (features), in elastic net regression, the optimization problem is formulated as $$\min_{\beta} \underbrace{\sum_{i=1}^{N}\left(y_i - \beta_0 - \sum_{i=1}^{p} x_{ij}\beta_j\right)^2}_{\text{Least Squares}} + \lambda \sum_{=1}^{p}\left(\underbrace{\frac{(1-\alpha)}{2}\beta_j^2}_{L_2 \text{ penalty}} + \underbrace{\alpha|\beta_j|}_{L_1 \text{ penalty}}\right),$$

where the parameter α determines the mix of the penalties (accepted value is α=0.5), and the parameter λ is the regularization tuning parameter, usually set using a cross validation procedure to optimize a performance criterion.

The regularization parameter λ, was chosen using K-fold cross validation (K=10) on the design dataset, as the one which yields minimum MSE between the prediction of the model and the desired response.

In validation phase, after the speech signal of a certain speaker was used in order to provide the three AHI estimates, $AHI_{SV}$, $AHI_{LT}$, and $AHI_{ST}$, the linear regression model was applied to provide the final fused AHI estimation $AHI_{FUS}$.

For the assessment of the system's (and its comprising subsystems) performance, Pearson correlation coefficient was used, mean AHI estimation error (MAE), and a diagnostic agreement. Diagnostic agreement is defined when the estimated AHI and the diagnosed AHI are both above 40 events/hr, or if the diagnosed AHI is less than 40 and the estimated AHI is within 10 events/hr from the diagnosed AHI. The diagnostic agreement is graphically described as a funnel. The motivation for using the diagnostic agreement measure is that small deviations between the system's AHI prediction and the diagnosed AHI value might be clinically unimportant, due to the fact that even the diagnosed value might vary in small fractions from one night to the other.

The selected features are summarized in the Tables 4-6 below.

TABLE 4 selected SVF

| Gender | Selection order | Phoneme | Frame-level descriptor | Functional |
|---|---|---|---|---|
| Male | 1 | /u/ | SPI | Arithmetic mean |
|  | 2 | /e/ | Spectral flatness | Geometric mean |
|  | 3 | /u/ | $\Delta MFCC_1$ | Zero-crossing rate |
|  | 4 | /o/ | $\Delta MFCC_1$ | Zero-crossing rate |
|  | 5 | /o/ | $\Delta MFCC_4$ | Inter-quantile range |
| Female | 1 | /o/ | $MFCC_5$ | Skewness |
|  | 2 | /a/ | Spectral flatness | Maximal value |
|  | 3 | /e/ | APQ3 | Arithmetic mean |
|  | 4 | /a/ | Shimmer | Quadratic mean |
|  | 5 | /i/ | $MFCC_{12}$ | $2^{nd}$ quartile |

TABLE 5

Selected LTF

| Gender | Selection order | Frame-level descriptor | Functional |
|---|---|---|---|
| Male | 1 | $\Delta\Phi^{(3)}$ | Arithmetic mean |
|  | 2 | $\Delta\Delta LPCC_1^{(1)}$ | Inter-quantile range |
|  | 3 | $LPCC_3^{(3)}$ | Variance |
|  | 4 | $LPCC_3^{(3)}$ | Inter-quantile range |
|  | 5 | $LPCC_3^{(1)}$ | Inter-quantile range |
| Female | 1 | $LPCC_4^{(3)}$ | Variance |
|  | 2 | $LPCC_4^{(1)}$ | Variance |
|  | 3 | $\Phi^{(3)}$ | Variance |
|  | 4 | $LPCC_1^{(2)}$ | Arithmetic mean |

TABLE 6

Selected STF

| Gender | Selection order | Feature symbol |
|---|---|---|
| Male | 1 | $GFCC_{10}$ |
|  | 2 | $\Delta c_9$ |
|  | 3 | $MHEC_{11}$ |
|  | 4 | $GFCC_7$ |
|  | 5 | $SWCE_3$ |
|  | 6 | $c_9$ |
| Female | 1 | $SWCE_{12}$ |
|  | 2 | $MHEC_7$ |
|  | 3 | $\Delta\Delta c_{12}$ |
|  | 4 | $\Delta\Delta c_{16}$ |

Figure 3:
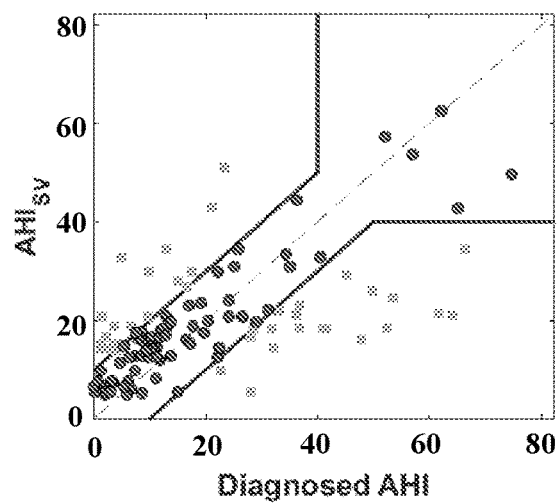
FIG. 3 demonstrates a correlation between performance of a system according to an embodiment of the invention and polysomnography.
Figure 3:
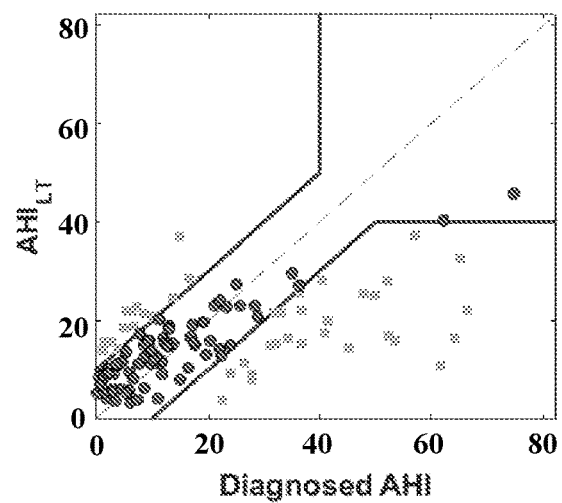
Figure 3:
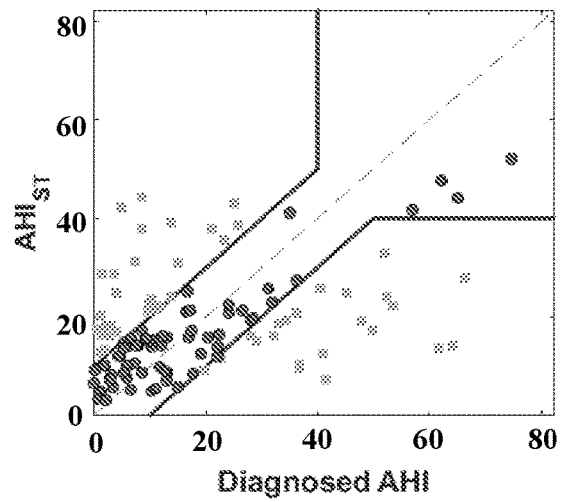
Figure 3:
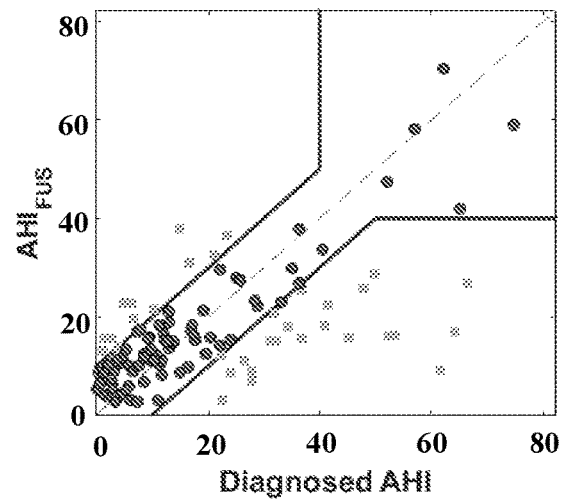

For the short-term subsystem, the order of the GMM-UBM was selected. Model orders of M=4 and M=8 were found most efficient for the male and female models, respectively. Moreover, the total-variability dimensions were of D=16 and D=9 were found as most efficient for the male and female models, respectively. Generally, for modern systems for speaker recognition/verification, which deploy GMM-UBM configuration and perform i-vector analysis, use much higher model orders (by two orders of magnitude), and also higher dimensions of the total variability subspace. These systems usually use databases which comprise an immense amount of speakers for training, and they are designed for recognition of certain speakers. The results are summarised in the FIG. 3. AHI estimation results for the male validation dataset (estimated AHI vs. diagnosed AHI) is shown. The dashed line represents identity line, and solid lines represent diagnostic agreement boundaries. Circles represent estimation results within the diagnostic agreement whereas squares represent the estimation that out of the diagnostic agreement. A—results for the sustained vowels subsystem, B—results for the long-term subsystem, C—results for the short-term subsystem, D—results for the fusion of the estimations performed by the three subsystems.

It can be seen that a significant correlation was obtained between the tested system and polysomnography results.

We claim:

1. A method for determining apnea-hypopnea index (AHI) estimation of a wake subject, said method comprising:
   obtaining an audio recorded phonogram signal comprising a speech segment and an audio recorded phonogram signal comprising a sustained-vowel segment;
   framing said signal comprising a sustained-vowel segment into frames;
   framing said signal comprising a speech segment into a set of long term frames and into a set of short term frames;
   generating one or more feature parameters for each short term frame, that are associated with short term characteristics and that are calculated according to the short term frame signal or according to a signal generated from the short term frame signal;
   generating one or more feature parameters for each long term frame, that are associated with long term characteristics and that are calculated according to the long term frame signal or according to a signal generated from the long term frame signal;
   generating one or more feature parameters for each sustained-vowel frame, that are associated with sustained-vowel characteristics and that are calculated according to the sustained-vowel frame signal or according to a signal generated from the sustained-vowel frame signal;
   applying a first computing system preformed model on the generated short term feature parameters to obtain a short term score;
   applying a second computing system preformed model on the generated long term feature parameters to obtain a long term score;
   applying a third computing system preformed model on the generated sustained-vowel feature parameters to obtain a sustained-vowel score; and
   applying a fusing model on the short term score and on the long term score and on the sustained-vowel score to obtain said subject's apnea-hypopnea index estimation;
   wherein the sustained-vowel segment comprises a subject's uttering of a vowel sound for a period of between 1 and 10 seconds; and
   wherein:
   (a) said one or more sustained vowel feature parameters comprise in a male subject at least one of: a "u:" phoneme arithmetic mean of soft phonation index (SPI), an "e" phoneme geometric mean of spectral flatness, a "u:" phoneme zero crossing rate of a first time derivative of Thomson multitaper mel-frequency $1^{st}$ cepstral coefficient $\Delta MFCC_1$, an "ɒ" phoneme zero crossing rate of a first time derivative of Thomson multitaper mel-frequency $2^{nd}$ cepstral coefficient $\Delta MFCC_2$, or an "ɒ" phoneme interquartile range of a first time derivative of Thomson multitaper mel-frequency $4^{th}$ cepstral coefficient $\Delta MFCC_4$; or
   (b) said one or more sustained vowel feature parameters in a female subject comprise at least one of an "ɒ" phoneme skewness of Thomson multitaper mel-frequency $5^{th}$ cepstral coefficient $MFCC_5$, an "a:" phoneme maximum of spectral flatness, an "e" phoneme arithmetic mean of 3-point amplitude perturbation quotient APQ3, an "a:" phoneme quadratic mean of shimmer, or an "i" phoneme second quartile of Thomson multitaper mel-frequency $12^{th}$ cepstral coefficient $MFCC_{12}$.

2. The method according to claim 1, further comprising carrying out a pre-processing stage comprising noise reduction of the signal comprising a speech segment and/or of the signal comprising a sustained-vowel segment.

3. The method of claim 1, further comprising obtaining a universal background Gaussian mixture model (GMM-UBN) vector comprising one or more short term feature parameters corresponding to the short term feature parameters generated for each subject, and modifying said GMM-UBN with the one or more short-term feature parameters generated for the subject to obtain a subject-specific distribution model vector;
   wherein the applying of a computing system preformed model on the generated one or more short term feature parameters comprises applying a computing system preformed model on said subject-specific distribution model vector to obtain the short term score.

4. The method according to claim 1, further comprising generating the computing system preformed models comprising:
   for each of a plurality of subjects, obtaining an audio recorded phonogram signal comprising a speech segment and an audio recorded phonogram signal comprising a sustained-vowel segment;
   for each subject, framing the signal comprising a sustained-vowel segment into frames;
   for each subject, framing the signal comprising a speech segment into a set of long term frames and into a set of short term frames;
   generating one or more feature parameters for each short term frame, that are associated with short term characteristics and that are calculated according to the short term frame signal or according to a signal generated from the short term frame signal;
   generating one or more feature parameters for each long term frame, that are associated with long term characteristics and that are calculated according to the long term frame signal or according to a signal generated from the long term frame signal;
   generating one or more feature parameters for each sustained-vowel frame, that are associated with sustained-vowel characteristics and that are calculated according to the sustained-vowel frame signal or according to a signal generated from the sustained-vowel frame signal;
   inputting the one or more generated short term feature parameters of each subject into a first machine learning computing system along with corresponding true result apnea-hypopnea index annotated AHI scores to generate the first computing system preformed model according to machine learning;
   inputting the generated long term parameters of each subject into a second machine learning computing system along with corresponding true result annotated AHI scores to generate the second computing system preformed model according to machine learning; and
   inputting the generated sustained-vowel parameters of each subject into a third machine learning computing system along with corresponding true result annotated AHI scores to generate the third computing system preformed model according to machine learning.

5. The method according to claim 4, further comprising obtaining a universal background Gaussian mixture model (GMM-UBN) vector comprising one or more short term feature parameters corresponding to the short term feature parameters generated for each subject; and modifying said GMM-UBN with said one or more short-term feature parameters generated for each subject to obtain a subject-specific distribution model vector for each subject;

wherein inputting the one or more generated short term feature parameters of each subject into a first machine learning computing system comprises inputting said subject-specific distribution model vector for each subject.

6. The method according to claim 1, wherein said one or more short term feature parameters in a male subject comprise at least one of gammatone-frequency $10^{th}$ cepstral coefficient ($GFCC_{10}$), first time derivative of Thomson multitaper mel-frequency $9^{th}$ cepstral coefficient ($\Delta c_9$), mean Hilbert envelope $11^{th}$ coefficient ($MHEC_{11}$), grammatone-frequency $7^{th}$ cepstral coefficient ($GFCC_7$), sine-wave cepstrum $3^{rd}$ estimator ($SWCE_3$) and Thomson multitaper mel-frequency $9^{th}$ cepstral coefficient ($c_9$).

7. The method according to claim 1, wherein said one or more short term feature parameters in a female subject comprise at least one of sine-wave cepstrum $12^{th}$ estimator $SWCE_{12}$, mean Hilbert envelope $7^{th}$ coefficient $MHEC_7$, second time derivative of Thomson multitaper mel-frequency $12^{th}$ coefficient $\Delta\Delta c_{12}$, and second time derivative of Thomson multitaper mel-frequency $16^{th}$ coefficient $\Delta\Delta c_{16}$.

8. The method according to claim 1, wherein said one or more long term feature parameters comprise in a male subject at least one of an arithmetic mean of a first time derivative of spectro-temporal energy belonging to a $3^{rd}$ modulation channel $\Delta\Phi^{(3)}$, an inter-quantile range of second time derivative of linear prediction $1^{st}$ cepstral coefficient belonging to a $1^{st}$ modulation channel $\Delta\Delta LPCC_1^{(1)}$, a variance of linear prediction cepstral coefficient belonging to a $3^{rd}$ modulation channel $LPCC_3^{(3)}$, an inter-quantile range of a $3^{rd}$ modulation channel $LPCC_3^{(3)}$, and an inter-quantile range of a $1^{st}$ modulation channel $LPCC_3^{(1)}$.

9. The method according to claim 1, wherein said one or more long term feature parameters in a female subject comprise at least one of a variance belonging to a $3^{rd}$ modulation channel of $LPCC_4^{(3)}$, a variance belonging to a $1^{st}$ modulation channel of $LPCC_4^{(1)}$, a variance of a spectro-temporal energy belonging to a $3^{rd}$ modulation channel $\Phi^{(3)}$, and an arithmetic mean belonging to a $2^{nd}$ modulation channel of $LPCC_1^{(2)}$.

10. A system for determining apnea-hypopnea index (AHI) estimation of a wake subject, comprising:
a processor;
a memory coupled to the processor storing program instructions executable by the processor to perform apnea-hypopnea index estimation of a wake subject, by performing operations comprising:
obtaining an audio recorded phonogram signal comprising a speech segment and an audio recorded phonogram signal comprising a sustained-vowel segment;
framing said signal comprising a sustained-vowel segment into frames;
framing said signal comprising a speech segment into a set of long term frames and into a set of short term frames;
generating one or more feature parameters for each short term frame, that are associated with short term characteristics and that are calculated according to the short term frame signal or according to a signal generated from the short term frame signal;
generating one or more feature parameters for each long term frame, that are associated with long term characteristics and that are calculated according to the long term frame signal or according to a signal generated from the long term frame signal;
generating one or more feature parameters for each sustained-vowel frame, that are associated with sustained-vowel characteristics and that are calculated according to the sustained-vowel frame signal or according to a signal generated from the sustained-vowel frame signal;
applying a first computing system preformed model on the generated one or more short term feature parameters to obtain a short term score;
applying a second computing system preformed model on the generated one or more long term feature parameters to obtain a long term score;
applying a third computing system preformed model on the generated sustained-vowel feature parameters to obtain a sustained-vowel score; and
applying a fusing model on the short term score and on the long term score and on the sustained-vowel score to obtain said subject's apnea-hypopnea index estimation;
wherein the sustained-vowel segment comprises a subject's uttering of a vowel sound for a period of between 1 and 10 seconds; and
wherein:
(a) said one or more sustained vowel feature parameters comprise in a male subject at least one of: a "u:" phoneme arithmetic mean of soft phonation index (SPI), an "e" phoneme geometric mean of spectral flatness, a "u:" phoneme zero crossing rate of a first time derivative of Thomson multitaper mel-frequency $1^{st}$ cepstral coefficient $\Delta MFCC_1$, an "ɒ" phoneme zero crossing rate of a first time derivative of Thomson multitaper mel-frequency $2^{nd}$ cepstral coefficient $\Delta MFCC_2$, or an "ɒ" phoneme inter-quartile range of a first time derivative of Thomson multitaper mel-frequency $4^{th}$ cepstral coefficient $\Delta MFCC_4$; or
(b) said one or more sustained vowel feature parameters in a female subject comprise at least one of an "ɒ" phoneme skewness of Thomson multitaper mel-frequency $5^{th}$ cepstral coefficient $MFCC_5$, an "a:" phoneme maximum of spectral flatness, an "e" phoneme arithmetic mean of 3-point amplitude perturbation quotient APQ3, an "a:" phoneme quadratic mean of shimmer, or an "i" phoneme second quartile of Thomson multitaper mel-frequency $12^{th}$ cepstral coefficient $MFCC_{12}$.

11. The system according to claim 10, wherein the program instructions are executable to perform further operations comprising carrying out a pre-processing stage comprising noise reduction of the signal comprising a speech segment and/or of the signal comprising a sustained-vowel segment.

12. The system according to claim 10, wherein the program instructions are executable to perform further operations comprising obtaining a universal background Gaussian mixture model (GMM-UBN) vector comprising one or more short term feature parameters corresponding to the short term feature parameters generated for each subject, and modifying said GMM-UBN with the one or more short-term feature parameters generated for each subject to obtain a subject-specific distribution model vector;

wherein the applying of a computing system preformed model on the generated one or more short term feature parameters comprises applying a computing system preformed model on said subject-specific distribution model vector to obtain the short term score.

13. The system according to claim 10, wherein said one or more short term feature parameters in a male subject comprise at least one of gammatone-frequency $10^{th}$ cepstral coefficient ($GFCC_{10}$), first time derivative of Thomson multitaper mel-frequency $9^{th}$ cepstral coefficient ($\Delta c_9$), mean Hilbert envelope $11^{th}$ coefficient ($MHEC_{11}$), grammatone-frequency $7^{th}$ cepstral coefficient ($GFCC_7$), sine-wave cepstrum $3^{rd}$ estimator ($SWCE_3$) and Thomson multitaper mel-frequency $9^{th}$ cepstral coefficient ($c_9$).

14. The system according to claim 10, wherein said one or more short term feature parameters in a female subject comprise at least one of sine-wave cepstrum $12^{th}$ estimator $SWCE_{12}$, mean Hilbert envelope $7^{th}$ coefficient $MHEC_7$, second time derivative of Thomson multitaper mel-frequency $12^{th}$ estimator $\Delta\Delta c_{12}$, and second time derivative of Thomson multitaper mel-frequency $16^{th}$ estimator $\Delta\Delta c_{16}$.

15. The system according to claim 10, wherein said one or more long term feature parameters in a male subject comprise at least one of an arithmetic mean of a first time derivative of spectro-temporal energy belonging to a $3^{rd}$ modulation channel $\Delta\Phi^{(3)}$, an inter-quantile range of second time derivative of linear prediction $1^{st}$ cepstral coefficient belonging to a $1^{st}$ modulation channel $\Delta\Delta LPCC_1^{(1)}$, a variance of linear prediction $3^{rd}$ cepstral coefficient belonging to a $3^{rd}$ modulation channel $LPCC_3^{(3)}$, an inter-quantile range of a $3^{rd}$ modulation channel $LPCC_3^{(3)}$, and an inter-quantile range of a $1^{st}$ modulation channel $LPCC_3^{(1)}$.

16. The system according to claim 10, wherein said one or more long term feature parameters in a female subject comprise at least one of a variance belonging to a $3^{rd}$ modulation channel of $LPCC_3^{(3)}$, a variance belonging to a $1^{st}$ modulation channel of $LPCC_4^{(1)}$, a variance of a spectro-temporal energy belonging to a $3^{rd}$ modulation channel $\Phi^{(3)}$, and an arithmetic mean belonging to a $2^{nd}$ modulation channel of $LPCC_1^{(2)}$.

* * * * *